United States Patent
Bendig et al.

(10) Patent No.: US 7,435,802 B2
(45) Date of Patent: *Oct. 14, 2008

(54) HUMANIZED ANTI-VLA4 IMMUNOGLOBULINS

(75) Inventors: Mary M. Bendig, West Hampsted (GB); Olivier J. Leger, Bertfordshire (GB); Jose Saldanha, Enfield (GB); Tarran S. Jones, Radlett (GB); Ted A. Yednock, Fairfax, CA (US)

(73) Assignee: Elan Pharaceuticals, Inc., South San Francisco, CA (US)

( * ) Notice: Subject to any disclaimer, the term of this patent is extended or adjusted under 35 U.S.C. 154(b) by 416 days.

This patent is subject to a terminal disclaimer.

(21) Appl. No.: 11/006,808

(22) Filed: Dec. 8, 2004

(65) Prior Publication Data

US 2006/0110394 A1    May 25, 2006

Related U.S. Application Data

(63) Continuation of application No. 09/155,739, filed as application No. PCT/US96/18807 on Nov. 21, 1996, now abandoned, and a continuation-in-part of application No. 08/561,521, filed on Nov. 21, 1995, now Pat. No. 5,840,299, which is a continuation-in-part of application No. 08/186,269, filed on Jan. 25, 1994, now abandoned, and a continuation-in-part of application No. PCT/US95/01219, filed on Jan. 25, 1995, now abandoned.

(51) Int. Cl.
*C07K 16/28* (2006.01)

(52) U.S. Cl. .............................. 530/388.73; 530/387.1; 530/387.3; 530/388.73; 530/388.22

(58) Field of Classification Search .................... None
See application file for complete search history.

(56) References Cited

U.S. PATENT DOCUMENTS 5,840,299 A * 11/1998 Bendig et al. ............ 424/133.1

* cited by examiner

*Primary Examiner*—Phillip Gambel
(74) *Attorney, Agent, or Firm*—Crowell & Moring LLP

(57) ABSTRACT

The invention provides methods of treatment using humanized immunoglobulins that specifically bind to alpha-4 integrin. The methods are useful for treatment of asthma, atherosclerosis, AIDS dementia, diabetes, inflammatory bowel disease, rheumatoid arthritis, transplant rejection, graft versus host disease, tumor metastasis, nephritis, atopic dermatitis, psoriasis, myocardial ischemia, and acute leukocyte mediated lung injury.

1 Claim, 16 Drawing Sheets

```
         atgagggcccctgctcagattttggattcttggtcaggagacgttgt
   1     -----------------------------------------------
         tactcccggggacgagtctaaaaacctaagaaccagtcctctgcaaca
ACTAGTCGACATGAGGGCCCCTGCTCAGTTTTTTGGCTTCTTG-3'
             A              A    C    AA
        MKV4 PRIMER agaaatgagaccgtctattcagttcctggggctcttgttgttctggcttcatgg
   49    -----------------------------------------------------
         tctttactctggcagataagtcaaggaccccgagaacaacaagaccgaagtacc

[M  R  P  S  I  Q  F  L  G  L  L  L  F  W  L  H  G
                                   LEADER tgctcagtgtgacatccagatgacacagtctccatcctcactgtctgcatctct
   103   -------------------------------------------------------
         acgagtcacactgtaggtctactgtgtcagaggtaggagtgacagacgtagaga A  Q  C][D  I  Q  M  T  Q  S  P  S  S  L  S  A  S  L
                                                          FR1
         gggaggcaaagtcaccatcacttgcaagacaagccaagacattaacaagtatat
   157   -----------------------------------------------------
         ccctccgtttcagtggtagtgaacgttctgttcggttctgtaattgttcatata G  G  K  V  T  I  T  C][K  T  S  Q  D  I  N  K  Y  M
                                                  CDR1 ggcttggtaccaacacaagcctggaaaacgtcctaggctgctcatacattacac
   211   -----------------------------------------------------
         ccgaaccatggttgtgttcggacctttgcaggatccgacgagtatgtaatgtg A][W  Y  Q  H  K  P  G  K  R  P  R  L  L  I  H][Y  T
                             FR2 atctgcattacagccaggcatcccatcaaggttcagtggaagtgggtctgggag
   265   -----------------------------------------------------
         tagacgtaatgtcggtccgtagggtagttccaagtcaccttcacccagaccctc

S  A  L  Q  P][G  I  P  S  R  F  S  G  S  G  S  G  R
             CDR2
```

*FIG. 1-1.*

```
     agattattccttcaacatcagcaacctggagcctgaagatattgcaacttatta
319  ------------------------------------------------------
     tctaataaggaagttgtagtcgttggacctcggacttctataacgttgaataat D   Y   S   F   N   I   S   N   L   E   P   E   D   I   A   T   Y   Y
               FR3 ttgtctacagtatgataatctgtggacgttcggtggaggcaccaagctggaaat
373  ------------------------------------------------------
     aacagatgtcatactattagacacctgcaagccacctccgtggttcgaccttta C] [L   Q   Y   D   N   L   W   T] [F   G   G   T   K   L   E   I
               CDR3                        FR4

MOUSE KAPPA PRIMER
                                3'-GTAGAAGGGTGGTAGGTGGGCCCT
     caaacgggctgatgctgcaccaactgtatccatcttcccaccatccacccggga
427  ------------------------------------------------------
     gtttgcccgactacgacgtggttgacataggtagaagggtggtaggtgggccct

K]

AGG-5'
     tcc
481  ---
     agg
```

FIG. 1-2.

```
              atgaaatgcagctgggtcatgttcttcctgatggcagtggttacaggg
       1      ------------------------------------------------
              tactttacgtcgacccagtacaagaaggactaccgtcaccaatgtccc
ACTAGTCGACATGAAATGCAGCTGGGTCATCTTCTTC-3′
                                       G
       MHV1 PRIMER
       [M  K  C  S  W  V  M  F  F  L  M  A  V  V  T  G
                             LEADER gtcaattcagaggttcagctgcagcagtctggggcagagcttgtgaagccaggg
       49     ------------------------------------------------------
              cagttaagtctccaagtcgacgtcgtcagacccgtctcgaacacttcggtccc V  N  S] [E  V  Q  L  Q  Q  S  G  A  E  L  V  K  P  G
                                                            FR1 gcctcagtcaagttgtcctgcacagcttctggcttcaacattaaagacacctat
       103    ------------------------------------------------------
              cggagtcagttcaacaggacgtgtcgaagaccgaagttgtaatttctgtggata A  S  V  K  L  S  C  T  A  S  G  F  N  I  K] [D  T  Y
                                                          CDR1 atacactgtgtgaagcagaggcctgaacagggcctggagtggattggaaggatt
       157    ------------------------------------------------------
              tatgtgacacacttcgtctccggacttgtcccggacctcacctaaccttcctaa I  H] [C  V  K  Q  R  P  E  Q  G  L  E  W  I  G] [R  I
                                 FR2 gatcctgcgaatggttatactaaatatgacccgaagttccagggcaaggccact
       211    ------------------------------------------------------
              ctaggacgcttaccaatatgatttatactgggcttcaaggtcccgttccggtga D  P  A  N  G  Y  T  K  Y  D  P  K  F  Q  G] [K  A  T
                       CDR2 ataacagctgacacatcctccaacacagcctacctgcagctcagcagcctgaca
       265    ------------------------------------------------------
              tattgtcgactgtgtaggaggttgtgtcggatggacgtcgagtcgtcggactgt I  T  A  D  T  S  S  N  T  A  Y  L  Q  L  S  S  L  T
                                                         FR3
```

*FIG. 2-1.*

```
        tctgaggacactgccgtctatttctgtgctagagagggatattatggtaactac
319     ------------------------------------------------------
        agactcctgtgacggcagataaagacacgatctctccctataataccattgatg S   E   D   T   A   V   Y   F   C   A   R] [E   G   Y   Y   G   N   Y
                                                                          CDR3 ggggtctatgctatggactactggggtcaaggaacctcagtcaccgtctcctca
373     ------------------------------------------------------
        ccccagatacgatacctgatgaccccagttccttggagtcagtggcagaggagt G   V   Y   A   M   D   Y] [W   G   Q   C   T   S   V   T   V   S   S]
                                    MOUSE GAMMA-1 PRIMER
                              3'-GTAGACAGATAGGTGACCGGGCCCTAGG-5
        gccaaaacgacacccccatctgtctatccactggcccgggatcc
427     --------------------------------------------
        cggttttgctgtgggggtagacagataggtgaccgggccctagg

```
            FR1                          CDR1                    FR2                    CDR2
        1          2          3                    4          5
     1234567890123 4567890123 4 5678901234 56789012345 6789 0123456
                  *           *********              *      ***
21.6 DIQMTQSPSSLSASLGGKVTITC KTSQDINKYMA WYQHKPGKRPRLLIH YTSALQP

REI  DIQMTQSPSSLSASVGDRVTITC QASQDIIKYLN WYQQTPGKAPKLLIY EASNLQA

La   DIQMTQSPSSLSASVGDRVTITC KTSQDINKYMA WYQQTPGKAPRLLIH YTSALQP

Lb   -------------------------------------------------R----- -------

FR3                        CDR3          FR4
       6          7          8          9         10
     7890123456789012345678901234567 8 901234567 8901234567
                              *                  *******
21.6 GIPSRFSGSGSGRDYSFNISNLEPEDIATYYC LQYDNL-WT FGGGTKLEIK

REI  GVPSRFSGSGSGTDYTFTISSLQPEDIATYYC QQYQSLPYT FGQGTKLQIT

La   GIPSRFSGSGSGRDYTFTISSLQPEDIATYYC LQYDNL-WT FGQGTKVEIK

```
              FR1                           CDR1              FR2                    CDR2
       1         2         3                          4          5              6
       1234567890123456789012345678901234567890  12345  6789012345678 9  012A34567890
                 ******                         ***                              ****

21.6   EVQLQQSGAELVKPGASVKLSCTASGFNIK           DTYIH  CVKQRPEQGLEWIG   RIDPANGYTKYDPKFQG
2*CL   QVQLVQSGAEVKKPGASVKVSCKASGYTFT           SYAMH  WVRQAPGQRLEWMG   WINAGNGNTKYSQKFQG
Ha     QVQLVQSGAEVKKPGASVKVSCKASGFNIK           DTYIH  WVRQAPGQRLEWMB   RIDPANGYTKYDPKFQG
Hb     ------------------------------           -----  ------G------   -----------------
Hc     ------------------------------           -----  -------------   -----------------

FR3                             CDR3             FR4
       6         7         8         9              10           11
       67890123456789012ABC34567890123 4  567890ABCDEF12  3456789 0123
                 *                                 *

21.6   KATITADTSSNTAYLQLSSLTSEDTAVYFCAR   EGYYGNYGVYAMDY  WGQGTLVTVSS
2*CL   RVTITRDTSASTAYMELSSLRSEDTAVYYCAR   GGYYGSGS---NY   WGQGTLVTVSS
Ha     RVTITADTSASTAYMELSSLRSEDTAVYYCAR   EGYYGNYGVYA DY  WGQGTLVTVSS
Hb     -----A--------------------------   -------------   -----------
Hc     -----A--------------------------   ---F---------   -----------
```

FIG. 7.

HindIII KOZAK SEQUENCE
```
    aagcttgccgccaccatgagaccgtctattcagttcctggggctcttgttgttc
1   ------------------------------------------------------
    ttcgaacggcggtggtactctggcagataagtcaaggaccccgagaacaacaag

[M  R  P  S  I  Q  F  L  G  L  L  L  F
                                       LEADER tggcttcatggtgctcagtgtgacatccagatgacacagtctccatcctcactg
55  ------------------------------------------------------
    accgaagtaccacgagtcacactgtaggtctactgtgtcagaggtaggagtgac W  L  H  G  A  Q  C][D  I  Q  M  T  Q  S  P  S  S  L
                                                      FR1 tctgcatctGTAggaGATAGAgtcaccatcacttgcaagacaagccaagacatt
109 ------------------------------------------------------
    agacgtagaCATcctCTATCTcagtggtagtgaacgttctgttcggttctgtaa S  A  S  V  G  D  R  V  T  I  T  C][K  T  S  Q  D  I
                                                      CDR1 aacaagtatatggcttggtaccaaCAGACAcctggaaaaGCTcctaggctgctc
163 ------------------------------------------------------
    ttgttcatataccgaaccatggttGTCTGTggaccttttCGAggatccgacgag N  K  Y  M  A][W  Y  Q  Q  T  P  G  K  A  P  R  L  L
                                      FR2 atacattacacatctgcattacagccaggcatcccatcaaggttcagtggaagt
217 ------------------------------------------------------
    tatgtaatgtgtagacgtaatgtcggtccgtagggtagttccaagtcaccttca

I  H][Y  T  S  A  L  Q  P][G  I  P  S  R  F  S  G  S
              CDR2 gggtctggagagattatACTttcACCatcagcAGCctgCAGcctgaagatatt
271 ------------------------------------------------------
    cccagaccctctctaataTGAaagTGGtagtcgTCGgacGTCggacttctataa G  S  F  R  D  Y  T  F  T  I  S  S  L  Q  P  E  D  I
                    FR3
```
FIG. 10-1.

```
      gcaacttattattgtctacagtatgataatctgtggacgttcggtCAAggcacc
325   ------------------------------------------------------
      cgttgaataataacagatgtcatactattagacacctgcaagccaGTTccgtgg A  T  Y  Y  C][L  Q  Y  D  N  L  W  T][F  G  Q  G  T
                          CDR3                         FR4

SPLICE DONOR SITE BamHI
      aagGTGgaaatcaaacgtgagtggatcc
379   ----------------------------
      ttcCACctttagtttgcactcacctagg

```
HindIII KOZAK SEQUENCE
      AAGCTTGCCGCCACCATGGACTGGACCTGGCGCGTGTTTTGCCTGCTCGCCGTG
1     ------------------------------------------------------
      TTCGAACGGCGGTGGTACCTGACCTGGACCGCGCACAAAACGGACGAGCGGCAC

[M  D  W  T  W  R  V  F  C  L  L  A  V
                                                    LEADER

GCTCCTGGGGCCCACAGCCAGGTGCAACTAGTGCAGTCCGGCGCCGAAGTGAAG
55    ------------------------------------------------------
      CGAGGACCCCGGGTGTCGGTCCACGTTGATCACGTCAGGCCGCGGCTTCACTTC

A  P  G  A  H  S][Q  V  Q  L  V  Q  S  G  A  E  V  K

AAACCCGGTGCTTCCGTGAAAGTCAGCTGTAAAGCTAGCGGTtttcaacattaaa
109   ------------------------------------------------------
      TTTGGGCCACGAAGGCACTTTCAGTCGACATTTCGATCGCCAaagttgtaattt

K  P  G  A  S  V  K  V  S  C  K  A  S  G  F  N  I  K][
              FR1 gacacctatatacacTGGGTTAGACAGGCCCCtGGCCAAaGGCTgGAGTGGATg
163   ------------------------------------------------------
      ctgtggatatatgtgACCCAATCTGTCCGGgGaCCGGTTtCCGAcCTCACCTAc D  T  Y  I  H][W  V  R  Q  A  P  G  Q  R  L  E  W  M
         CDR1                          FR2
```

FIG. 11-1.

```
      GGaaggattgatcctgcgaatggttatactaaatatgacccgaagttccagggc
217   ------------------------------------------------------
      CCttcctaactaggacgcttaccaatatgatttatactgggcttcaaggtcccg G][R   I   D   P   A   N   G   Y   T   K   Y   D   P   K   F   Q   G][
                                    CDR2 cgggtcACCatcACCgcaGACACCTCTgccagcACCGCCTACATGGAACTGTCC
271   ------------------------------------------------------
      gcccagTGGtagTGGcgtCTGTGGAGAcggtcgTGGCGGATGTACCTTGACAGG R   V   T   I   T   A   D   T   S   A   S   T   A   Y   M   E   L   S
                                                                        FR3

AGCCTGCGCTCCGAGGACACTGCAGTCTACTACTGCGCCagagagggatattat
325   ------------------------------------------------------
      TCGGACGCGAGGCTCCTGTGACGTCAGATGATGACGCGGtctctccctataata

S   L   R   S   E   D   T   A   V   Y   Y   C   A   R][E   G   Y   Y ggtaactacggggtctatgctatgGACTAcTGGGGtCAaGGaACCCTTGTCACC
379   ------------------------------------------------------
      ccattgatgccccagatacgatacCTGATgACCCCaGTtCCtTGGGAACAGTGG G   N   Y   G   V   Y   A   M   D   Y][W   G   Q   G   T   L   V   T
        CDR3                                                         FR4

SPLICE DONOR SITE BamHI
      GTCtccTCAGGTGAGTGGATCC
433   ----------------------
      CAGaggAGTCCACTCACCTAGG

V   S   S]
                        FIG. 11-2.
```

HUMANIZED ANTI-VLA4 IMMUNOGLOBULINS

CROSSREFERENCE TO RELATED APPLICATIONS

This application is a continuation of U.S. patent application Ser. No. 09/155,739, filed Sep. 11, 1998 now abandoned, which is a national phase entry under 35 U.S.C. § 371 of International Application No. PCT/US96/18807, filed Nov. 21, 1996 and is a continuation-in-part of application Ser. No. 08/561,521, filed Nov. 21, 1995, now U.S. Pat. No. 5,840, 299, which is a continuation-in-part of application Ser. No. 08/186,269, filed Jan. 25, 1994, now abandoned, and is a continuation-in-part of PCT/US95/01219, filed Jan. 25, 1995, now abandoned.

TECHNICAL FIELD

This invention relates generally to humanized antibodies specific for the alpha-4 (α4) integrin and therapeutic uses of the same.

BACKGROUND OF THE INVENTION

Inflammation is a response of vascularized tissues to infection or injury and is effected by adhesion of leukocytes to the endothelial cells of blood vessels and their infiltration into the surrounding tissues. In normal inflammation, the infiltrating leukocytes release toxic mediators to kill invading organisms, phagocytize debris and dead cells, and play a role in tissue repair and the immune response. However, in pathologic inflammation, infiltrating leukocytes are over-responsive and can cause serious or fatal damage. See, e.g., Hickey, *Psychoneuroimmunology II* (Academic Press 1990).

The attachment of leukocytes to endothelial cells is effected via specific interaction of cell-surface ligands and receptors on endothelial cells and leukocytes. See generally Springer, *Nature* 346:425-433 (1990). The identity of the ligands and receptors varies for different cell subtypes, anatomical locations and inflammatory stimuli. The VLA-4 leukocyte cell-surface receptor was first identified by Hemler, EP 330,506 (1989) (incorporated by reference in its entirety for all purposes). VLA-4 is a member of the β1 integrin family of cell surface receptors, each of which comprises α and β chains. VLA-4 contains an α4 chain and a β1 chain. VLA-4 specifically binds to an endothelial cell ligand termed VCAM-1. See Elices et al., *Cell* 60:577-584 (1990) (incorporated by reference in its entirety for all purposes). The α4 chain also associates with a β7 chain to form an integrin referred to as α4β7. Although VCAM-1 was first detected on activated human umbilical vein cells, this ligand has also been detected on brain endothelial cells. See commonly owned, co-pending application U.S. Ser. No. 07/871,223 (incorporated by reference in its entirety for all purposes).

Adhesion molecules such as α4 integrin are potential targets for therapeutic agents. The VLA-4 receptor of which α4 integrin is a subunit is a particularly important target because of its interaction with a ligand residing on brain endothelial cells. Diseases and conditions resulting from brain inflammation have particularly severe consequences. For example, one such disease, multiple sclerosis (MS), has a chronic course (with or without exacerbations and remissions) leading to severe disability and death. The disease affects an estimated 250,000 to 350,000 people in the United States alone.

Antibodies against α4 integrin have been tested for their anti-inflammatory potential both in vitro and in vivo in animal models. See U.S. Ser. No. 07/871,223 and Yednock et al., *Nature* 356:63-66 (1992) (incorporated by reference in its entirety for all purposes). The in vitro experiments demonstrate that α4 integrin antibodies block attachment of lymphocytes to brain endothelial cells. The animal experiments test the effect of α4 integrin antibodies on animals having an artificially induced condition (experimental autoimmune encephalomyelitis), simulating multiple sclerosis. The experiments show that administration of anti-α4 integrin antibodies prevents inflammation of the brain and subsequent paralysis in the animals. Collectively, these experiments identify anti-α4 integrin antibodies as potentially useful therapeutic agents for treating multiple sclerosis and other inflammatory diseases and disorders.

A significant problem with the anti-α4 integrin antibodies available to-date is that they are all of murine origin, and therefore likely to raise a human anti-mouse response (HAMA) in clinical use. A HAMA response reduces the efficacy of mouse antibodies in patients and prevents continued administration. One approach to this problem is to humanize mouse antibodies. In this approach, complimentarily determining regions (CDRs) and certain other amino acids from donor mouse variable regions are grafted into human variable acceptor regions and then joined to human constant regions. See, e.g., Riechmann et al., *Nature* 332:323-327 (1988); Winter, U.S. Pat. No. 5,225,539 (1993) (each of which is incorporated by reference in its entirety for all purposes).

Although several examples of humanized antibodies have been produced, the transition from a murine to a humanized antibody involves a compromise of competing considerations, the solution of which varies with different antibodies. To minimize immunogenicity, the immunoglobulin should retain as much of the human acceptor sequence as possible. However, to retain authentic binding properties, the immunoglobulin framework should contain sufficient substitutions of the human acceptor sequence to ensure a three-dimensional conformation of CDR regions as close as possible to that in the original mouse donor immunoglobulin. As a result of these competing considerations, many humanized antibodies produced to-date show some loss of binding affinity compared with the corresponding murine antibodies from which they are derived. See, e.g., Jones et al., *Nature* 321:522-525 (1986); Shearman et al., *J. Immunol.* 147:4366-4373 (1991); Kettleborough et al., *Protein Engineering* 4:773-783 (1991); Gorman et al., *Proc. Natl. Acad. Sci. USA* 88:4181-4185 (1991); Tempest et al., *Biotechnology* 9:266-271 (1991).

Based on the foregoing it is apparent that a need exists for humanized anti-α4 integrin antibodies demonstrating a strong affinity for α4 integrin, while exhibiting little, if any, human-antimousei response. The present invention fulfill this and other needs.

SUMMARY OF THE INVENTION

The invention provides uses of a humanized antibody to alpha-4 integrin in the manufacture of a medicament for treating a disease selected from the group consisting of asthma, atherosclerosis, AIDS dementia, diabetes, inflammatory bowel disease, rheumatoid arthritis, transplant rejection, graft versus host disease, tumor metastasis, nephritis, atopic dermatitis, psoriasis, myocardial ischemia, and acute leukocyte mediated lung injury.

The humanized immunoglobulins used in the above methods specifically bind to a alpha-4 integrin. The humanized antibodies comprise a humanized light chain and a humanized heavy chain. A preferred humanized light chain comprises three complimentarily determining regions (CDR1, CDR2 and CDR3) having amino acid sequences from the corresponding complimentarily determining regions of a mouse 21-6 immunoglobulin light chain, and a variable region framework from a human kappa light chain variable region framework sequence except in at least one position selected from a first group consisting of positions L45, L49, L58 and L69, wherein the amino acid position is occupied by the same amino acid present in the equivalent position of the mouse 21-6 immunoglobulin light chain variable region framework. A preferred humanized heavy chain comprises three complimentarily determining regions (CDR1, CDR2 and CDR3) having amino acid sequences from the corresponding complimentarily determining regions of a mouse 21-6 immunoglobulin heavy chain, and a variable region framework from a human heavy chain variable region framework sequence except in at least one position selected from a group consisting of H27, H28, H29, H30, H44, H71, wherein the amino acid position is occupied by the same amino acid present in the equivalent position of the mouse 21-6 immunoglobulin heavy chain variable region framework. The immunoglobulins specifically bind to alpha-4 integrin with an affinity having a lower limit of about $10^7$ $M^{-1}$ and an upper limit of about five times the affinity of the mouse 21-6 immunoglobulin.

Usually, the humanized light and heavy chain variable region frameworks are from RE1 and 21/28'CL variable region framework sequences respectively. When the humanized light chain variable region framework is from RE1, at least two framework amino acids are replaced. One amino acid is from the first group of positions described supra. The other amino acids is from a third group consisting of positions L104, L105 and L107. This position is occupied by the same amino acid present in the equivalent position of a kappa light chain from a human immunoglobulin other than RE1.

Some humanized immunoglobulins have a mature light chain variable region sequence designated La or Lb in FIG. 6, or a mature heavy chain variable region sequence designated Ha, Hb or Hc in FIG. 7. Preferred humanized immunoglobulins include those having an La light chain and an Ha, Hb or Hc heavy chain.

In another aspect the invention provides pharmaceutical compositions for use in treating the above diseases. The pharmaceutical compositions comprise a humanized immunoglobulin or binding fragment as described supra, and a pharmaceutically acceptable carrier. In some methods of treatment a therapeutically effective amount of a pharmaceutical composition is administered to a patient suffering from one of the diseases listed above.

BRIEF DESCRIPTION OF FIGURES

FIG. 1: DNA (SEQ. ID NO:1) and amino acid (SEQ. ID NO:2) sequences of the mouse 21.6 light chain variable region.

FIG. 2: DNA (SEQ. ID NO:3) and amino acid (SEQ. ID NO:4) sequences of the mouse 21.6 heavy chain variable region.

FIG. 6: Comparisons of the amino acid sequences of mouse and reshaped human 21.6 (SEQ. ID NO:5) light chain variable regions. The amino acid residues that are part of the Chothia canonical sequences for the CDR loop structures are marked with an asterisk. REI (SEQ. ID NO:6) shows the FRs and CDRs from the $V_L$ region of human REI light chain. La (SEQ. ID NO:7) and Lb (SEQ. ID NO:8) are the two versions of reshaped human 21.6 $V_L$ region. The residues in the FRs of La that differ from those in the REI sequence are underlined. In Lb, only the residues in the framework regions that differ from those of REI are shown.

FIG. 7: Comparisons of the amino acid sequences of the mouse and reshaped human 21.6 (SEQ. ID NO:9) heavy chain variable regions. The amino acid residues that are part of the canonical sequences for the Chothia CDR loop structures are marked with an asterisk. 2*CL (SEQ. ID NO:10) shows the FRs and CDRs from the $V_H$ region of human 21/28'CL antibody. Ha (SEQ. ID NO:11), Hb (SEQ. ID NO:12), and Hc (SEQ. ID NO:13) are the three versions of reshaped human 21.6 $V_H$ region. The residues in the FRs of Ha that differ from those in the 21/28'CL sequence are underlined. In Hb and Hc, only the residues in the framework regions that differ from those of 21/28'CL are shown.

FIG. 10: cDNA and amino acid sequences (SEQ. ID NOS: 14 and 15) of the first version ("a") of reshaped human 21.6 light chain variable region.

FIG. 11: DNA and amino acid sequences (SEQ. ID NOS: 16 and 17) of the first version ("a") of reshaped human 21.6 heavy chain variable region.

Definitions

Figure 3A:
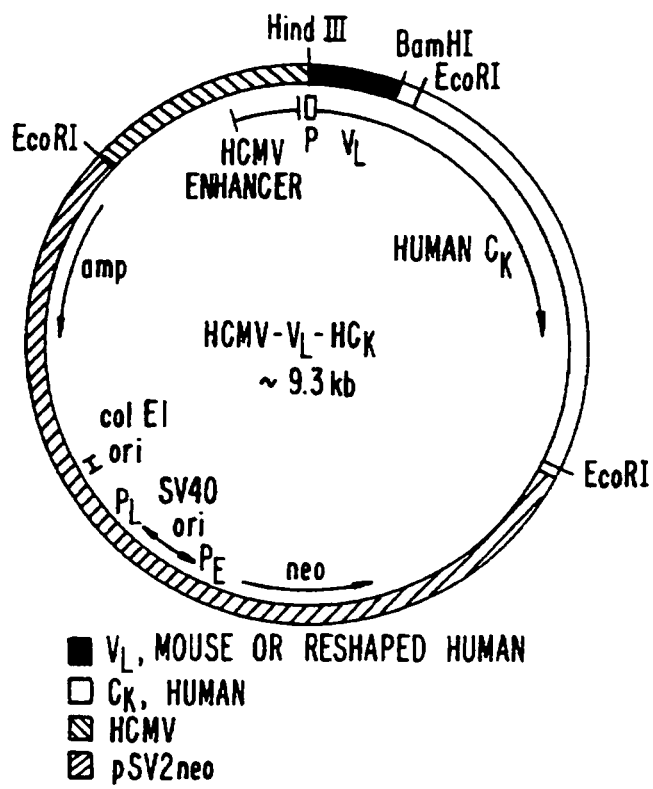
FIG. 3: Light (A) and heavy (B) chain expression vectors used to produce chimeric and reshaped human antibodies with human kappa light chains and human gamma-1 heavy chains in mammalian cells.

Abbreviations for the twenty naturally occurring amino acids follow conventional usage (*Immunology—A Synthesis* (2nd ed., E. S. Golub & D. R. Gren, eds., Sinauer Associates, Sunderland, M A, 1991)). Stereoisomers (e.g., D-amino acids) of the twenty conventional amino acids, unnatural amino acids such as α,α-disubstituted amino acids, N-alkyl amino acids, lactic acid, and other unconventional amino acids may also be suitable components for polypeptides of the present invention. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysinei, ω-N-methylarginine, and other similar amino acids and imino acids (e.g., 4-hydroxyproline). Moreover, amino acids may be modified by glycosylation, phosphorylation and the like.

In the polypeptide notation used herein, the lefthand direction is the amino terminal direction and the righthand direction is the carboxy-terminal direction, in accordance with standard usage and convention. Similarly, unless specified otherwise, the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences."

The phrase "polynucleotide sequence" refers to a single or double-stranded polymer of deoxyribonucleotide or ribonucleotide bases read from the 5' to the 3' end. It includes self-replicating plasmids, infectious polymers of DNA or RNA and non-functional DNA or RNA.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, such as a polynucleotide sequence of FIG. 1 or 2, or may comprise a complete DNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci.* (*USA*) 85:2444 (1988) (each of which is incorporated by reference in its entirety for all purposes), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of sequence similarity over the comparison window) generated by the various methods is selected. The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, the sequence shown in FIG. 1 or 2.

As applied to polypeptides, the term "sequence identity" means peptides share identical amino acids at corresponding positions. The term "sequence similarity" means peptides have identical or similar amino acids (i.e., conservative substitutions) at corresponding positions. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions. The term "substantial similarity" means that two peptide sequences share corresponding percentages of sequence similarity.

The term "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species.

For purposes of classifying amino acids substitutions as conservative or nonconservative, amino acids are grouped as follows: Group I (hydrophobic sidechains): norleucine, met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for another.

Amino acids from the variable regions of the mature heavy and light chains of immunoglobulins are designated Hx and Lxx respectively, where x is a number designating the position of an amino acids according to the scheme of Kabat et al., *Sequences of Proteins of Immunological Interest* (National Institutes of Health, Bethesda, Md. (1987) and (1991)) (hereinafter collectively referred to as "Kabat et al.," incorporated by reference in their entirety for all purposes). Kabat et al. list many amino acid sequences for antibodies for each subclass, and list the most commonly occurring amino acid for each residue position in that subclass. Kabat et al. use a method for assigning a residue number to each amino acid in a listed sequence, and this method for assigning residue numbers has become standard in the field. Kabat et al.'s scheme is extendible to other antibodies not included in the compendium by aligning the antibody in question with one of the consensus sequences in Kabat et al. The use of the Kabat et al. numbering system readily identifies amino acids at equivalent positions in different antibodies. For example, an amino acid at the L50 position of a human antibody occupies the equivalence position to an amino acid position L50 of a mouse antibody.

DETAILED DESCRIPTION

I. Humanized Antibodies Specific for Alpha-4 Integrin

In one embodiment of the invention, humanized immunoglobulins (or antibodies) specific for the alpha-4 integrin, a subunit of VLA-4 are provided. The humanized immunoglobulins have variable framework regions substantially from a human immunoglobulin (termed an acceptor immunoglobulin) and complimentarily determining regions substantially from a mouse immunoglobulin termed mu MAb 21.6 (referred to as the donor immunoglobulin). The constant region(s), if present, are also substantially from a human immunoglobulin. The humanized antibodies exhibit a specific binding affinity for alpha-4 integrin of at least $10^7$, $10^8$, $10^9$, or $10^{10}$ $M^{-1}$. Usually the upper limit of binding affinity of the humanized antibodies for alpha-4 integrin is within a factor of three or five of that of mu MAb 21.6 (about $10^9$ $M^{-1}$). Often the lower limit of binding affinity is also within a factor of three or five of that of mu MAb 21.6.

A. General Characteristics of Immunoglobulins

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (See generally, *Fundamental Immunology* (Paul, W., ed., 2nd ed. Raven Press, N.Y., 1989), Ch. 7 (incorporated by reference in its entirety for all purposes).

The variable regions of each light/heavy chain pair form the antibody binding site. The chains all exhibit the same general structure of relatively conserved framework regions (FR) joined by three hypervariable regions, also called complimentarily determining regions or CDRS. The CDRs from the two chains of each pair are aligned by the framework regions, enabling binding to a specific epitope. CDR and FR residues are delineated according to the standard sequence definition of Kabat et al., supra. An alternative structural definition has been proposed by Chothia et al., *J. Mol. Biol.* 196:901-917 (1987); *Nature* 342:878-883 (1989); and *J. Mol. Biol.* 186:651-663 (1989) (hereinafter collectively referred to as "Chothia et al." and incorporated by reference in their entirety for all purposes). When framework positions, as defined by Kabat et al., supra, that constitute structural loop positions as defined by Chothia et al., supra, the amino acids present in the mouse antibody are usually incorporated into the humanized antibody.

B. Production of Humanized Antibodies (1) Mouse MAb 21.6

The starting material for production of humanized antibodies is mu MAb 21.6. The isolation and properties of this antibody are described in U.S. Ser. No. 07/871,223. Briefly, mu MAb 21.6 is specific for the alpha-4 integrin and has been shown to inhibit human lymphocyte binding to tissue cultures of rat brain cells stimulated with tumor necrosis factor. The cloning and sequencing of cDNA encoding the mu MAb 21.6 antibody heavy and light chain variable regions is described in Example 1, and the nucleotide and predicted amino acids sequences are shown in FIGS. 1 and 2. These figures also illustrate the subdivision of the amino acid coding sequencing into framework and complimentarily determining domains. From N-terminal to C-terminal, both light and heavy chains comprise the domains FR1, CDR1, FR2, CDR2, FR3, CDR3 and FR4. The assignment of amino acids to each domain is in accordance with the numbering convention of Kabat et al., supra.

(2) Selection of Human Antibodies to Supply Framework Residues

The substitution of mouse CDRs into a human variable domain framework is most likely to result in retention of their correct spatial orientation if the human variable domain framework adopts the same or similar conformation to the mouse variable framework from which the CDRs originated. This is achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., *Protein Engineering* 4:773 (1991); Kolbinger et al., *Protein Engineering* 6:971 (1993).

Suitable human antibody sequences are identified by computer comparisons of the amino acid sequences of the mouse variable regions with the sequences of known human antibodies. The comparison is performed separately for heavy and light chains but the principles are similar for each. This comparison reveals that the mu 21.6 light chain shows greatest sequence identity to human light chains of subtype kappa 1, and that the mu 21.6 heavy chain shows greatest sequence identity to human heavy chains of subtype one, as defined by Kabat et al., supra. Thus, light and heavy human framework regions are usually derived from human antibodies of these subtypes, or from consensus sequences of such subtypes. The preferred light and heavy chain human variable regions showing greatest sequence identity to the corresponding regions from mu MAb 21.6 are from antibodies RE1 and 21/28'CL respectively.

(3) Computer Modeling

Figure 5:
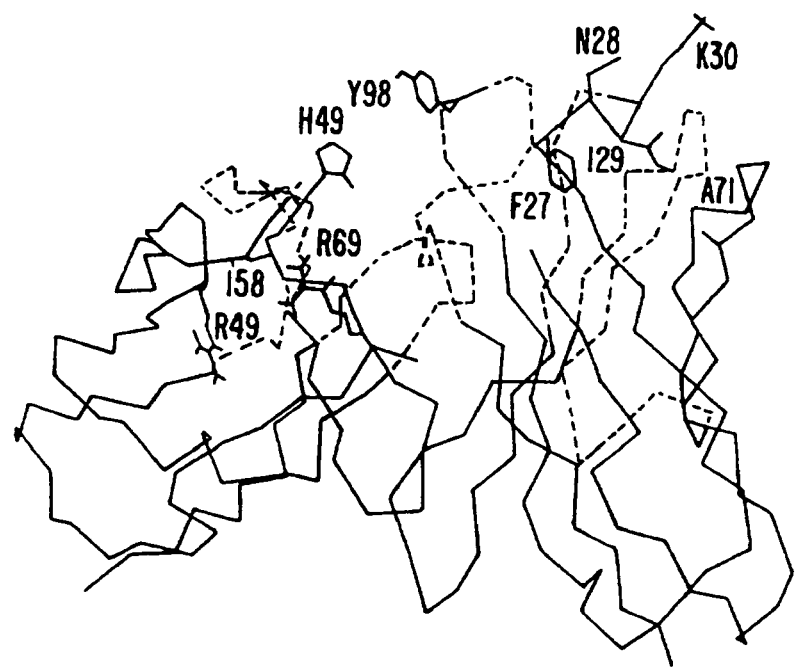
FIG. 5: Molecular model of the variable regions of mouse 21.6 antibody. Residues of special interest are ladeled.

The unnatural juxtaposition of murine CDR regions with human variable framework region can result in unnatural conformational restraints, which, unless corrected by substitution of certain amino acid residues, lead to loss of binding affinity. The selection of amino acid residues for substitution is determined, in part, by computer modeling. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity is/are selected as starting points for construction of the molecular model. For example, for the light chain of mu MAb 21.6, the starting point for modeling the framework regions, CDR1 and CDR2 regions, was the human light chain RE1. For the CDR3 region, the starting point was the CDR3 region from the light chain of a different human antibody HyHEL-5. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits. Example 4 discusses in more detail the steps taken to produce a three dimensional computer model for the variable regions of the mu MAb 21.6, and the model is shown in FIG. 5. This model can in turn serve as a starting point for predicting the three-dimensional structure of an antibody containing the mu MAb 21.6 complimentarily determining regions substituted in human framework structures. Additional models can be constructed representing the structure when further amino acid substitutions to be discussed infra, are introduced.

(4) Substitution of Amino Acid Residues

As noted supra, the humanized antibodies of the invention comprise variable framework regions substantially from a human immunoglobulin and complimentarily determining regions substantially from a mouse immunoglobulin termed mu MAb 21.6. Having identified the complimentarily determining regions of mu MAb 21.6 and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a HAMA response in humans. Amino acids are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

When an amino acid differs between a mu MAb 21.6 variable framework region and an equivalent human variable framework region, the human framework amino acid should usually be substituted by the equivalent mouse amino acid if it is reasonably expected that the amino acid:

(1) noncovalently binds antigen directly (e.g., amino acids at positions L49, L69 of mu MAb 21.6), (2) is adjacent to a CDR region, is part of a CDR region under the alternative definition proposed by Chothia et al., supra, or otherwise interacts with a CDR region (e.g., is within about 3 Å of a CDR region) (e.g., amino acids at positions L45, L58, H27, H28, H29, H30 and H71 of mu MAb 21.6), or (3) participates in the $V_L$-$V_H$ interface (e.g., amino acids at position H44 of mu MAb 21.6).

Other candidates for substitution are acceptor human framework amino acids that are unusual for a human immunoglobulin at that position (e.g., amino acids at positions L104, L105 and L107 of mu MAb 21.6). These amino acids can be substituted with amino acids from the equivalent position of more typical human immunoglobulins. Alternatively, amino acids from equivalent positions in the mouse MAb 21.6 can be introduced into the human framework regions when such amino acids are typical of human immunoglobulin at the equivalent positions.

In general, substitution of all or most of the amino acids fulfilling the above criteria is desirable. Occasionally, however, there is some ambiguity about whether a particular amino acid meets the above criteria, and alternative variant immunoglobulins are produced, one of which has that particular substitution, the other of which does not. The humanized antibodies of the present invention will usually contain a substitution of a human light chain framework residue with a corresponding mu MAb 21.6 residue in at least 1, 2 or 3, and more usually 4, of the following positions: L45, L49, L58 and L69. The humanized antibodies also usually contain a substitution of a human heavy chain framework residue in at least 1, 2, 3, 4, or 5, and sometimes 6, of the following positions: H27, H28, H29, H30, H44 and H71. Optionally, H36 may also be substituted. In preferred embodiments when the human light chain acceptor immunoglobulin is RE1, the light chain also contains substitutions in at least 1 or 2, and more usually 3, of the following positions: L104, L105 and L107. These positions are substituted with the amino acid from the equivalent position of a human immunoglobulin having a more typical amino acid residues. Appropriate amino acids to substitute are shown in FIGS. 6 and 7.

Usually the CDR regions in humanized antibodies are substantially identical, and more usually, identical to the corresponding CDR regions in the mu MAb 21.6 antibody. Occasionally, however, it is desirable to change one of the residues in a CDR region. For example, Example 5 identifies an amino acid similarity between the mu MAb 21.6 CDR3 and the VCAM-1 ligand. This observation suggests that the binding affinity of humanized antibodies might be improved by redesigning the heavy chain CDR3 region to resemble VCAM-1 even more closely. Accordingly, one or more amino acids from the CDR3 domain can be substituted with amino acids from the VCAM-1 binding domain. Although not usually desirable, it is sometimes possible to make one or more conservative amino acid substitutions of CDR residues without appreciably affecting the binding affinity of the resulting humanized immunoglobulin.

Other than for the specific amino acid substitutions discussed above, the framework regions of humanized immunoglobulins are usually substantially identical, and more usually, identical to the framework regions of the human antibodies from which they were derived. Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin. However, in general, such substitutions are undesirable.

(5) Production of Variable Regions

Having conceptually selected the CDR and framework components of humanized immunoglobulins, a variety of methods are available for producing such immunoglobulins. Because of the degeneracy of the code, a variety of nucleic acid sequences will encode each immunoglobulin amino acid sequence. The desired nucleic acid sequences can be produced by de novo solid-phase DNA synthesis or by PCR mutagenesis of an earlier prepared variant of the desired polynucleotide. Oligonucleotide-mediated mutagenesis is a preferred method for preparing substitution, deletion and insertion variants of target polypeptide DNA. See Adelman et al., *DNA* 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

(6) Selection of Constant Region

The variable segments of humanized antibodies produced as described supra are typically linked to at least a portion of an immunoglobulin constant region (Fc), typically that of a human immunoglobulin. Human constant region DNA sequences can be isolated in accordance with well-known procedures from a variety of human cells, but preferably immortalized B-cells (see Kabat et al., supra, and WO87/02671) (each of which is incorporated by reference in its entirety for all purposes). Ordinarily, the antibody will contain both light chain and heavy chain constant regions. The heavy chain constant region usually includes CH1, hinge, CH2, CH3, and CH4 regions.

The humanized antibodies include antibodies having all types of constant regions, including IgM, IgG, IgD, IgA and IgE, and any isotype, including IgG1, IgG2, IgG3 and IgG4. When it is desired that the humanized antibody exhibit cytotoxic activity, the constant domain is usually a complement-fixing constant domain and the class is typically $IgG_1$. When such cytotoxic activity is not desirable, the constant domain may be of the $IgG_2$ class. The humanized antibody may comprise sequences from more than one class or isotype.

(7) Expression Systems

Nucleic acids encoding humanized light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Such control sequences include a signal sequence, a promoter, an enhancer, and a transcription termination sequence. Expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362.)

*E. coli* is one prokaryotic host useful particularly for cloning the polynucleotides of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see Winnacker, *From Genes to Clones* (VCH Publishers, N.Y., N.Y., 1987). Eukaryotic cells are actually preferred, because a number of suitable host cell lines capable of secreting intact immunoglobulins have been developed in the art, and include the CHO cell lines, various Cos cell lines, HeLa cells, preferably myeloma cell lines, or transformed B-cells or hybridomas. Expression vectors for these cells can include expression control sequences, such as an origin of replication, a promoter, and an enhancer (Queen et al., *Immunol. Rev.* 89:49-68 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See generally Sambrook et al., *Molecular Cloning: A Laboratory Manual* (Cold Spring Harbor Press, 2nd ed., 1989) (incorporated by reference in its entirety for all purposes). When heavy and light chains are cloned on separate expression vectors, the vectors are co-transfected to obtain expression and assembly of intact immunoglobulins.

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see generally Scopes, *Protein Purification* (Springer-Verlag, N.Y., 1982). Substantially pure immunoglobulins of at least about 90 to 95% homogeneity are preferred, and 98 to 99% or more homogeneity most preferred, for pharmaceutical uses.

C. Fragments of Humanized Antibodies

In another embodiment of the invention, fragments of humanized antibodies are provided. Typically, these fragments exhibit specific binding to alpha-4 integrin with an affinity of at least $10^7 M^{-1}$, and more typically $10^8$ or $10^9 M^{-1}$. Humanized antibody fragments include separate heavy chains, light chains Fab, Fab' F(ab')$_2$, Fabc, and Fv. Fragments are produced by recombinant DNA techniques, or by enzymic or chemical separation of intact immunoglobulins.

II. Nucleic Acids

The humanized antibodies and fragments thereof are usually produced by expression of nucleic acids. All nucleic acids encoding a humanized antibody or a fragment thereof described in this application are expressly included in the invention.

III. Computers

In another aspect of the invention, computers programmed to display three dimensional images of antibodies on a monitor are provided. For example, a Silicon Graphics IRIS 4D workstation running under the UNIX operating system and using the molecular modeling package QUANTA (Polygen Corp. USA) is suitable. Computers are useful for visualizing models of variants of humanized antibodies. In general, the antibodies of the invention already provide satisfactory binding affinity. However, it is likely that antibodies with even stronger binding affinity could be identified by further variation of certain amino acid residues. The three dimensional image will also identify many noncritical amino acids, which could be the subject of conservative substitutions without appreciable affecting the binding affinity of the antibody. Collectively even conservative substitutions can have a significant effect on the properties of an immunoglobulin. However, it is likely many individual conservative substitutions will not significantly impair the properties of the immunoglobulins.

IV. Testing Humanized Antibodies

The humanized antibodies of the invention are tested by a variety of assays. These include a simple binding assay for detecting the existence or strength of binding of an antibody to cells bearing VLA-4 of which one subunit is alpha-4 integrin. The antibodies are also tested for their capacity to block the interaction of cells bearing the VLA-4 receptor with endothelial cells expressing a VCAM-1 ligand. The endothelial cells may be grown and stimulated in culture or may be a component of naturally occurring brain tissue sections. See Yednock et al., supra, and U.S. Ser. No. 07/871,223. The humanized antibodies are also tested for their capacity to prevent or reduce inflammation and subsequent paralysis in laboratory animals having experimental autoimmune encephalomyelitis (EAE). EAE is induced by injection of a laboratory animal with $CD4^+$ T-cells specific for myelin basic protein or by directly immunizing animals with myelin basic protein. This protein is localized in the central nervous system, and the reactive T-cells initiate destruction of sheaths containing this protein in a manner that simulates the autoimmune response in multiple sclerosis. See Yednock et al., supra, and copending U.S. Ser. No. 07/871,223.

V. Pharmaceutical Compositions

The invention provides pharmaceutical compositions to be used for prophylactic or therapeutic treatment comprising an active therapeutic agent, i.e., a humanized 21.6 antibody or a binding fragment thereof, and a variety of other components. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

For parenteral administration, the antibodies of the invention can be administered as injectionable dosages of a solution or suspension of the substance in a physiologically acceptable diluent with a pharmaceutical carrier which can be a sterile liquid such as water and oils with or without the addition of a surfactant and other pharmaceutically preparations are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. The antibodies of this invention can be administered in the form of a depot injection or implant preparation which can be formulated in such a manner as to permit a sustained release of the active ingredient. A preferred composition comprises monoclonal antibody at 5 mg/mL, formulated in aqueous buffer consisting of 50 mM L-histidine, 150 mM NaCl, adjusted to pH 6.0 with HCl.

VI. Methods of Diagnosis

The humanized antibodies and their binding fragments are useful for detecting the presence of cells bearing alpha-4 integrin. The presence of such cells in the brain is diagnostic of an inflammatory response and may signal the need for commencement of a therapeutic method discussed infra. Diagnosis can be accomplished by removing a cellular sample from a patient. The amount of expressed alpha-4 integrin in individual cells of the sample is then determined, e.g., by immunohistochemical staining of fixed cells or by Western blotting of a cell extract with a humanized MAb 21.6 antibody or a binding fragment thereof.

Diagnosis can also be achieved by in vivo administration of a labeled humanized MAb 21.6 (or binding fragment) and detection by in vivo imaging. The concentration of humanized MAb 21.6 administered should be sufficient that the binding to cells having the target antigen is detectable compared to the background signal. The diagnostic reagent can be labeled with a radioisotope for camera imaging, or a paramagnetic isotope for magnetic resonance or electron spin resonance imaging.

A change (typically an increase) in the level of alpha-4 integrin in a cellular sample or imaged from an individual, which is outside the range of clinically established normal levels, may indicate the presence of an undesirable inflammatory response reaction in the individual from whom the sample was obtained, and/or indicate a predisposition of the individual for developing (or progressing through) such a reaction. Alpha-4 integrin can also be employed as a differentiation marker to identify and type cells of certain lineages and developmental origins. Such cell-type specific detection can be used for histopathological diagnosis of undesired immune responses.

VII. Methods of Treatment

The invention also provides methods of treatment that exploit the capacity of humanized MAb 21.6 to block α4-dependent interactions. The α4-dependent interaction with the VCAM-1 ligand on endothelial cells is an early event in many inflammatory responses, including those of the central nervous system. Undesired diseases and conditions resulting from inflammation and having acute and/or chronic clinical exacerbations include multiple sclerosis (Yednock et al., *Nature* 356, 63 (1992); Baron et al., *J. Exp. Med.* 177, 57 (1993)), meningitis, encephalitis, stroke, other cerebral traumas, inflammatory bowel disease including ulcerative colitis and Crohn's disease (Hamann et al., *J. Immunol.* 152, 3238 (1994)), (Podolsky et al., *J. Clin. Invest.* 92, 372 (1993)), rheumatoid arthritis (van Dinther-Janssen et al., *J. Immunol.* 147, 4207 (1991); van Dinther-Janssen et al., *Annals Rheumatic Diseases* 52, 672 (1993); Elices et al., *J. Clin. Invest.* 93, 405 (1994); Postigo et al., *J. Clin. Invest.* 89, 1445 (1992), asthma (Mulligan et al., *J. Immunol.* 150, 2407 (1993)) and acute juvenile onset diabetes (Type 1) (Yang et al., *PNAS* 90, 10494 (1993); Burkly et al., *Diabetes* 43, 529 (1994); Baron et al., *J. Clin. Invest.* 93, 1700 (1994)), AIDS dementia (Sasseville et al., *Am. J. Path.* 144, 27 (1994); atherosclerosis (Cybulsky & Gimbrone, Science 251, 788, L1 et al., *Arterioscler. Thromb.* 13, 197 (1993)), nephritis (Rabb et al., *Springer Semin. Immunopathol.* 16, 417-25 (1995)), retinitis, atopic dermatitis, psoriasis, myocardial ischemia and acute leukocyte-mediated lung injury such as occurs in adult respiratory distress syndrome.

Inflammatory bowel disease is a collective term for two similar diseases referred to as Crohn's disease and ulcerative colitis. Crohn's disease is an idiopathic, chronic ulcerocon-strictive inflammatory disease characterized by sharply delimited and typically transmural involvement of all layers of the bowel wall by granulomatous inflammatory reaction. Any segment of the gastrointestinal tract, from the mouth to the anus, may be involved, although the disease most commonly affects the terminal ileum and/or colon. Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involved the wrists, elbows, ankles and knees. The arthritis results from interaction of synovial cells with leukocytes that infiltrate from the circulation into the synovial lining of joints. See e.g., Paul, *Immunology* (3d ed., Raven Press, 1993).

Another indication for humanized antibodies against alpha-4 integrin is in treatment of organ or graft rejection. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. $CD8^+$ cells, $CD4^+$ cells and monocytes are all involved in the rejection of transplant tissues. Antibodies directed to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420-425 (1996); Georczynski et al., *Immunology* 87, 573-580 (1996); Georcyznski et al., *Transplant. Immunol.* 3, 55-61 (1995); Yang et al., *Transplantation* 60, 71-76 (1995); Anderson et al., *APMIS* 102, 23-27 (1994).

A related use for antibodies to alpha-4 integrin is in modulating the immune response involved in "graft versus host" disease (GVHD). See e.g., Schlegel et al., *J. Immunol.* 155, 3856-3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bond marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of humanized antibodies of the invention is inhibiting tumor metastasis. Several tumor cells have been reported to express alpha-4 integrin and antibodies to alpha-4 integrin have been reported to block adhesion of such cells to endothelial cells. Steinback et al., *Urol. Res.* 23, 175-83 (1995); Orosz et al., *Int. J. Cancer* 60, 867-71 (1995); Freedman et al., *Leuk. Lymphoma* 13, 47-52 (1994); Okahara et al., *Cancer Res.* 54, 3233-6 (1994).

A further use of the claimed antibodies is in treating multiple sclerosis. Multiple sclerosis is a progressive neurological autoimmune disease that affects an estimated 250,000 to 350,000 people in the United States. Multiple sclerosis is thought to be a the result of a specific autoimmune reaction in which certain leukocytes attack and initiate the destruction of myelin, the insulating sheath covering nerve fibers. In an animal model for multiple sclerosis, murine monoclonal antibodies directed against alpha-4-beta-1 integrin have been shown to block the adhesion of leukocytes to the endothelium, and thus prevent inflammation of the central nervous system and subsequent paralysis in the animals.

The humanized MAb 21.6 antibodies of the present invention offer several advantages over the mouse antibodies already shown to be effective in animals models:

1) The human immune system should not recognize the framework or constant region of the humanized antibody as foreign, and therefore the antibody response against such an injected antibody should be less than against a totally foreign mouse antibody or a partially foreign chimeric antibody.

2) Because the effector portion of the humanized antibody is human, it may interact better with other parts of the human immune system.

3) Injected mouse antibodies have been reported to have a half-life in the human circulation much shorter than the half-life of normal human antibodies (Shaw et al., *J. Immunol.*

138:4534-4538 (1987)). Injected humanized antibodies have a half-life essentially equivalent to naturally occurring human antibodies, allowing smaller and less frequent doses.

The pharmaceutical compositions discussed supra can be administered for prophylactic and/or therapeutic treatments of the previously listed inflammatory disorders, including multiple sclerosis, inflammatory bowel disease, asthma, atherosclerosis, rheumatoid arthritis, organ or graft rejection and graft versus host disease. In therapeutic applications, compositions are administered to a patient suspected of, or already suffering from such a disease in an amount sufficient to cure, or at least partially arrest, the symptoms of the disease and its complications. An amount adequate to accomplish this is defined as a therapeutically- or pharmaceutically-effective dose.

In prophylactic applications, pharmaceutical compositions are administered to a patient susceptible to, or otherwise at risk of, a particular disease in an amount sufficient to eliminate or reduce the risk or delay the outset of the disease. Such an amount is defined to be a prophylactically effective dose. In patients with multiple sclerosis in remission, risk may be assessed by NMR imaging or, in some cases, by presymptomatic indications observed by the patient.

The pharmaceutical compositions will be administered by parenteral, topical, intravenous, oral, or subcutaneous, intramuscular local administration, such as by aerosol or transdermally, for prophylactic and/or therapeutic treatment. Although the proteinaceous substances of this invention may survive passage through the gut following oral administration, subcutaneous, intravenous, intramuscular, intraperitoneal administration by depot injection; or by implant preparation, are preferred.

The pharmaceutical compositions can be administered in a variety of unit dosage forms depending upon the method of administration. For example, unit dosage forms suitable for oral administration include powder, tablets, pills, capsules, and lozenges.

Effective doses of the compositions of the present invention, for the treatment of the above described conditions will vary depending upon many different factors, including means of administration, target site, physiological state of the patient, and other mendicants administered. Thus, treatment dosages will need to be titrated to optimize safety and efficacy. These compositions may be administered to mammals for veterinary use and for clinical use in humans in a manner similar to other therapeutic agents, i.e., in a physiologically acceptable carrier. In general, the administration dosage will range from about 0.0001 to 100 mg/kg, and more usually 0.01 to 5 mg/kg of the host body weight.

In a preferred treatment regime, the antibody is administered by intravenous infusion or subcutaneous injection at a dose from 1 to 5 mg antibody per kilo of bodyweight. The dose is repeated at interval from 2 to 8 weeks. Within this range, the preferred treatment regimen is 3 mg antibody per kilo of bodyweight repeated at a 4 week interval.

The humanized antibodies of the invention can be used with effective amounts of other therapeutic agents against acute and chronic inflammation. Such agents include antibodies and other antagonists of adhesion molecules, including other integrins, selectins, and immunoglobulin (Ig) superfamily members (see Springer, *Nature* 346, 425-433 (1990); Osborn, *Cell* 62, 3 (1990); Hynes, *Cell* 69, 11 (1992)). Integrins are heterodimeric transmembrane glycoproteins consisting of an a chain (120-180 kDa) and a β chain (90-110 kDa), generally having short cytoplasmic domains. For example, three important integrins, LFA-1, Mac-1 and P150, 95, have different alpha subunits, designated CD11a, CD11b and CD11c, and a common beta subunit designated CD18. LFA-1 ($\alpha_L\beta_2$) is expressed on lymphocytes, granulocyte and monocytes, and binds predominantly to an Ig-family member counter-receptor termed ICAM-1 and related ligands. ICAM-1 is expressed on many cells, including leukocytes and endothelial cells, and is up-regulated on vascular endothelium by cytokines such as TNF and IL-1. Mac-1 ($\alpha_M\beta_2$) is distributed on neutrophils and monocytes, and also binds to ICAM-1. The third β2 integrin, P150,95 ($\alpha_X\beta_2$), is also found on neutrophils and monocytes. The selectins consist of L-selectin, E-selectin and P-selectin.

Other antiinflammatory agents that can be used in combination with the antibodies against alpha-4 integrin include antibodies and other antagonists of cytokines, such as interleukins IL-1 through IL-13, tumor necrosis factors α & β, interferons α, β and γ, tumor growth factor Beta (TGF-β), colony stimulating factor (CSF) and granulocyte monocyte colony stimulating factor (GM-CSF). Other antiinflammatory agents include antibodies and other antagonists of chemokines such as MCP-1, MIP-1α, MIP-1β, rantes, exotaxin and IL-8. Other antiinflammatory agents include NSAIDS, steroids and other small molecule inhibitors of inflammation. Formulations, routes of administration and effective concentrations of agents for combined therapies are as described above for the humanized antibodies against alpha-4 integrin.

VIII. Other Uses

The humanized antibodies are also useful for affinity purification of alpha-4 integrin. The antibodies are immobilized to a solid support and a solution of dispersed proteins is passed over the support. Alpha-4 integrin and associated β chain bind to the support and is thereby separated from other proteins. The purified alpha-4 integrin or a fragment thereof, made available by this method, can be used as a vaccine or as an immunogen for producing further antibodies.

The humanized antibodies of the invention are also useful for generating idiotypic antibodies by, for example, immunization of an animal with a humanized antibody. An anti-idiotype antibody whose binding to the human antibody is inhibited by alpha-4 integrin or fragments thereof is selected. Because both the anti-idiotypic antibody and the alpha-4 integrin or fragments thereof bind to the humanized immunoglobulin, the anti-idiotypic antibody may represent the "internal image" of an epitope and thus may substitute a ligand of alpha-4 integrin, i.e., VCAM-1.

EXAMPLES

Example 1

Cloning and Sequencing of the Mouse 21.6 Variable Regions

The mouse anti-alpha-4 integrin antibody 21.6 has been described in co-pending application U.S. Ser. No. 07/871, 223. Total RNA was isolated from hybridoma cells producing mouse 21.6 antibody. First-strand cDNA was synthesized using a kit (Pharmacia Biosystems Limited). Heavy and light chain variable regions were obtained by using PCR primers designed to hybridize to sequences flanking and external to the sequences coding for the variable regions, thereby allowing cloning of the entire coding sequences for the mouse 21.6 antibody variable regions. Sense PCR primers hybridizing to the 5'-ends of mouse kappa light-chain leader sequences and of mouse heavy-chain leader sequences were designed based on databases of 42 mouse kappa light-chain leader sequences and of 55 mouse heavy-chain leader sequences (Jones & Bendig, *Bio/Technology* 9:88-89 (1991) (incorporated by reference in its entirety for all purposes)). These primers were used in conjunction with anti-sense PCR primers hybridizing to the 3'-ends of the mouse constant regions (kappa or gamma).

Mouse 21.6 kappa $V_L$ regions were PCR-amplified in a 50 µl reaction typically containing 10 mM Tris-HCl (pH 8.3), 50 mM KCl, 200 µM dNTPs, 1.5 mM $MgCl_2$, 1 unit of AmpliTaq (Perkin Elmer Cetus) DNA polymerase, 1 µl of cDNA template, 0.25 µM of MKV primer and 0.25 µM of mouse kappa light chain anti-sense PCR primer (FIG. 1). Mouse 21.6 $V_H$ regions were PCR-amplified as described above except that MHVH primer and an anti-sense PCR primer specific for the mouse IgG1 heavy chain constant region were used (FIG. 2). Each PCR reaction was cycled, after an initial melt at 94° C. for 5 min, at 94° C. for 1 min, 55° C. for 1 min, and 72° C. for 2 min over 25 cycles. The completion of the last cycle was followed by a final extension at 72° C. for 10 min. The ramp time between the primer-annealing and extension steps was 2.5 min. Following PCR amplification, 10 µl aliquots from each reaction were analyzed on ethidium-bromide-stained 1.5% agarose gels.

The PCR products were cloned using the "TA Cloning System" (Invitrogen Corporation). Vectors containing inserts of the correct size were sequenced using double-stranded plasmid DNA and Sequenase (United States Biochemical Corporation). To avoid any errors that might have been introduced during the PCR amplification steps, at least two independently PCR-amplified and cloned DNA fragments were sequenced for each variable region.

The sequences of PCR products were compared with other mouse light chain and heavy chain variable regions (see Tables 1 and 2). This comparison indicated that the PCR products from MKV2 and MKV4 primers represent authentic mouse 21.6 kappa variable regions, and those from MHV1 and MHV2 primers represent authentic mouse $V_H$ regions, and it was concluded that the sequences of these product are those of the mouse 21.6 antibody variable regions. The DNA and amino acid sequences of the cDNA coding for the mouse 21.6 $V_L$ and $V_H$ regions are shown in FIGS. 1 and 2.

TABLE 1

Comparison of the mouse 21.6 light chain variable region to other light chain variable regions.

| Mouse 21.6 $V_L$ versus: | Percent Similarity[1] | Percent Identity |
|---|---|---|
| Consensus sequence for mouse kappa $V_L$ subgroup 5[2] | 84.0 | 72.6 |
| Consensus sequence for human kappa $V_L$ subgroup 1[2] | 84.0 | 69.8 |
| Consensus sequence for human kappa $V_L$ subgroup 2[2] | 65.1 | 52.8 |
| Consensus sequence for human kappa $V_L$ subgroup 3[2] | 72.6 | 57.5 |
| Consensus sequence for human kappa $V_L$ subgroup 4[2] | 72.6 | 58.5 |

TABLE 1-continued

Comparison of the mouse 21.6 light chain variable region to other light chain variable regions.

| Mouse 21.6 $V_L$ versus: | Percent Similarity[1] | Percent Identity |
|---|---|---|
| Sequence of $V_L$ from human REI[3] (Member of human kappa $V_L$ subgroup 1) | 81.0 | 72.4 |

[1]Percent similarity was determined using the "GAP" program of the University of Wisconsin Genetics Computer Group.
[2]Consensus sequences were taken from Kabat et al., supra.
[3]REI as sequenced by Palm et al., Hoppe-Seyler's Z. Physiol. Chem. 356: 167-191 (1975).

TABLE 2

Comparison of the mouse 21.6 heavy chain variable region to other heavy chain variable regions.

| Mouse 21.6 $V_H$ versus: | Percent Similarity[1] | Percent Identity |
|---|---|---|
| Consensus sequence for mouse $V_H$ subgroup 2c[2] | 94.3 | 91.1 |
| Consensus sequence for human $V_H$ subgroup 1[2] | 78.0 | 65.0 |
| Consensus sequence for human $V_H$ subgroup 2[2] | 70.5 | 53.3 |
| Consensus sequence for human $V_H$ subgroup 3[2] | 67.5 | 52.8 |
| Sequence of $V_H$ from human 21/28'CL[3] (Member of human $V_H$ subgroup 1) | 76.5 | 64.7 |

[1]Percent similarity was determined using the "GAP" program of the University of Wisconsin Genetics Computer Group.
[2]Consensus sequences were taken from Kabat et al., supra.
[3]21/28'CL as sequenced by Dersimonian et al., J. Immunol. 139: 2496-2501 (1987).

Example 2

Construction of Chimeric 21.6 Antibody

Figure 3B:
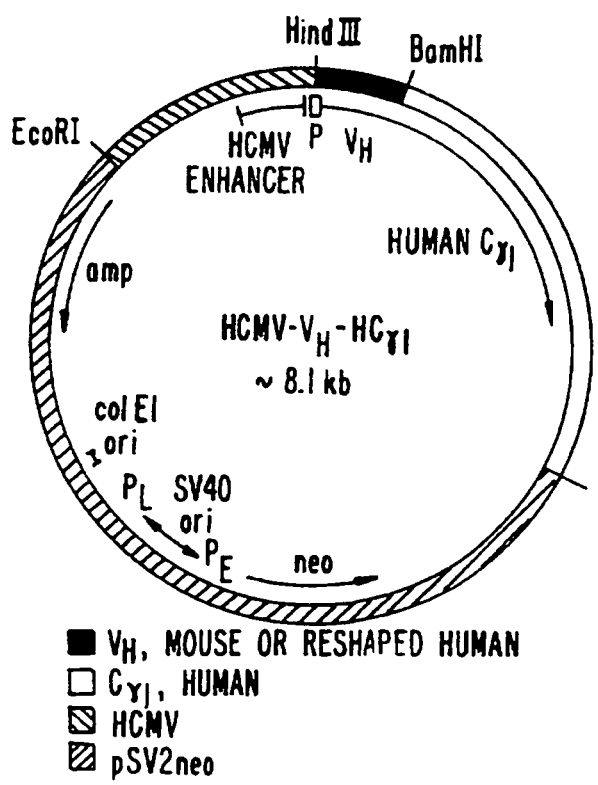

Chimeric light and heavy chains were constructed by linking the PCR-cloned cDNAs of mouse 21.6 $V_L$ and $V_H$ regions to human constant regions. The 5'- and 3'-ends of the mouse cDNA sequences were modified using specially designed PCR primers. The 5'-end PCR-primers (Table 3), which hybridize to the DNA sequences coding for the beginnings of the leader sequences, were designed to create the DNA sequences essential for efficient translation (Kozak, *J. Mol. Biol.* 196:947-950 (1987)), and to create a HindIII restriction sites for cloning into an expression vector. The 3'-end primers (Table 3), which hybridize to the DNA sequences coding for the ends of J regions, were designed to create the DNA sequences essential for splicing to the constant regions, and to create a BamHI site for cloning into an expression vector. The products of PCR amplification were digested with HindIII and BamHI, cloned into a pUC19 vector, and sequenced to confirm that no errors had occurred during PCR amplification. The adapted mouse 21.6 variable regions were then subcloned into mammalian cells expression vectors containing either the human kappa or gamma-1 constant regions (FIG. 3).

TABLE 3

PCR primers for the construction
of chimeric 21.6 antibody.

A. Light chain variable region

1. Primer for reconstruction of the 5'-end (37mer)
(SEQ. ID NO: 18)

```
5' C AGA AAG CTT GCC GCC ACC ATG AGA CCG TCT ATT CAG 3'
        HindIII Kozak      M   R   P   S   I   Q
                Consensus
                Sequence
```

2. Primer for reconstruction of the 3'-end (35mer) (SEQ. ID
NO: 19)

```
5' CC GAG GAT CCA CTC ACG TTT GAT TTC CAG CTT GGT 3'
      BamHI  Splice donor site
```

B. Heavy chain variable region

1. Primer for reconstruction of the 5'-end (37mer) (SEQ. ID
NO: 20)

```
5' C AGA AAG CTT GCC GCC ACC ATG AAA TGC AGC TGG GTC 3'
        HindIII Kozak      M   K   C   S   W   V
                Consensus
                Sequence
```

2. Primer for reconstruction of the 3'-end (33mer) (SEQ. ID
NO: 21)

```
5' CC GAG GAT CCA CTC ACC TGA GGA GAC GGT GAC T 3'
      BamHI  Splice donor site
```

Example 3

Expression and Analysis of 21.6 Chimeric Antibody

Figure 4:
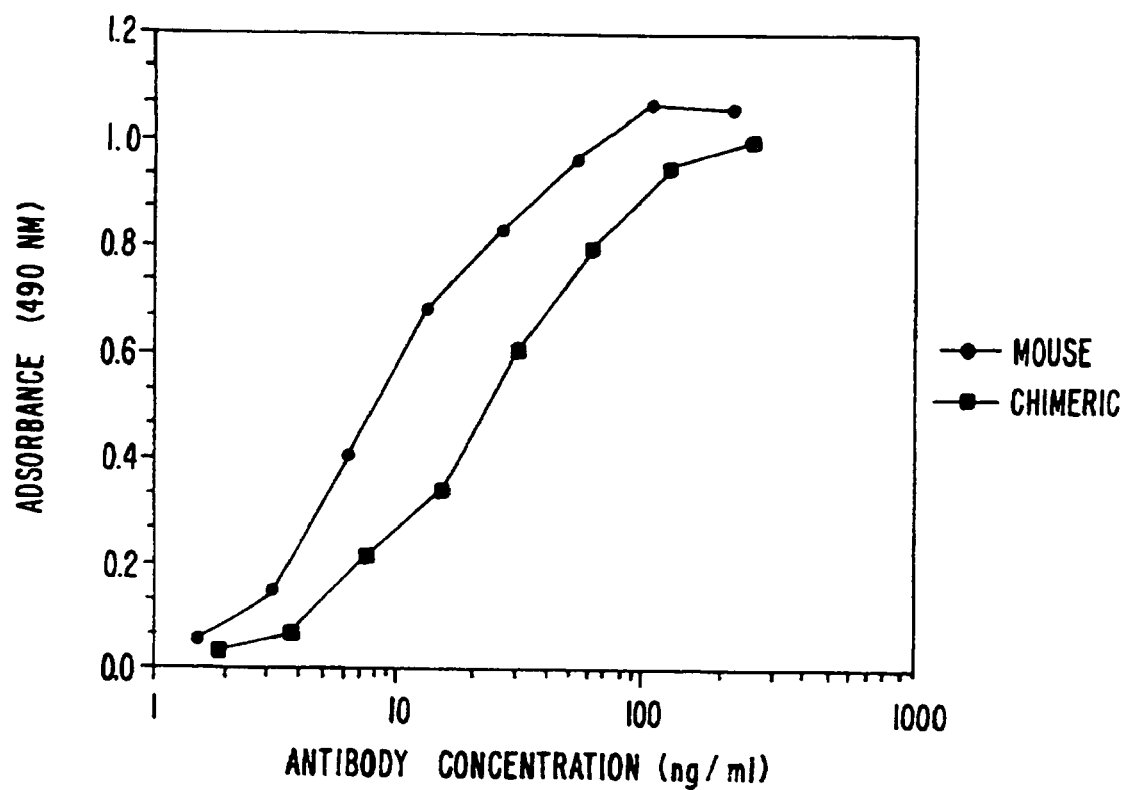
FIG. 4: ELISA comparison of chimeric and mouse 21.6 antibody binding to L cells expressing human α4β1 integrin on their surface.
Figure 12A:
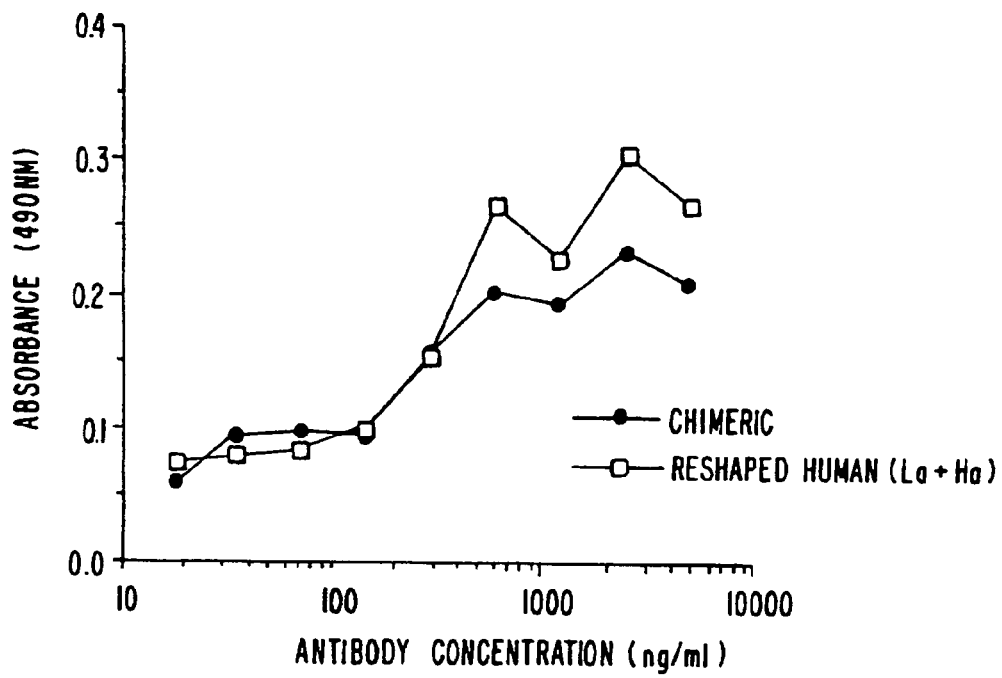
FIG. 12: ELISA comparison of chimeric and reshaped human 21.6 antibodies to bind to L cells expressing human α4β1 integrin on their surface.
Figure 12B:
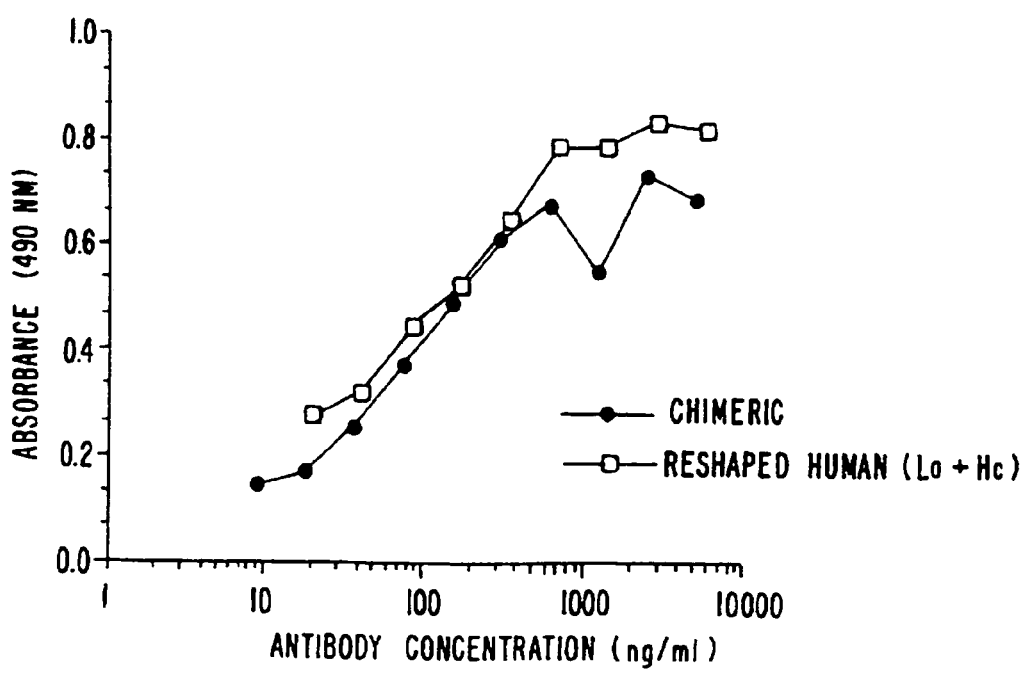
Figure 13A:
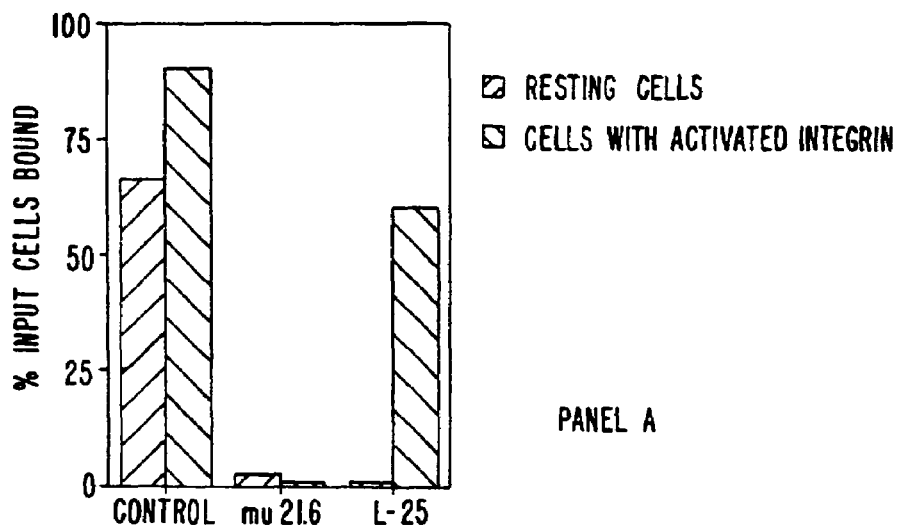
FIG. 13: Comparison of mouse 21.6 antibody with a different anti-alpha-4 integrin antibody, L25. Panel A compares the ability of the antibodies to block binding of U937 monocytic cells to purified VCA-1 in the presence and absence of $Mn^{2+}$. Panel B compares the ability of the antibodies to block binding of Jurkat cells to increasing concentrations of VCAM-1.
Figure 13B:
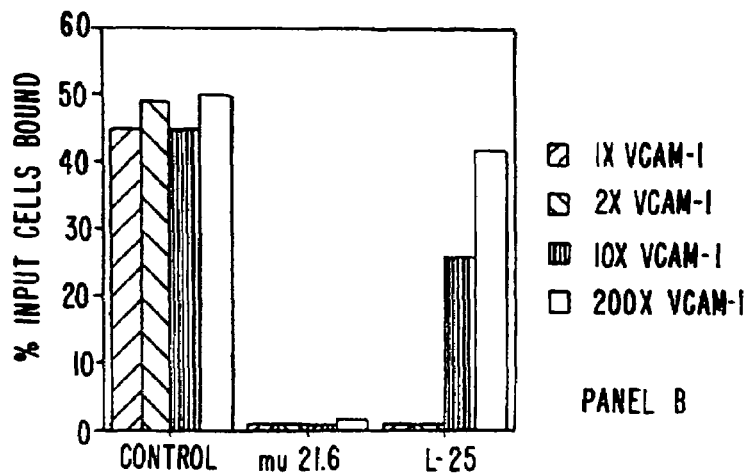

The two plasmid DNAs coding for the chimeric 21.6 light and heavy chains were cotransfected into Cos cells. After two or three days, media from the Cos cells was analyzed by ELISA (1) for the production of a human IgG-like antibody and (2) for the ability of this human-like antibody to bind to L cells expressing human α4β1 integrin on their surface. FIGS. 4 and 12 show analyses of unpurified and protein-A purified samples of chimeric 21.6 antibody for binding to human α4β1 integrin, in comparison with purified mouse 21.6 antibody control. These figures show that the chimeric 21.6 antibody bound well to antigen and confirm that the correct mouse 21.6 $V_L$ and $V_H$ regions had been cloned.

Example 4

Modeling the Structure of the Mouse 21.6 Variable Regions

A molecular model of the $V_L$ and $V_H$ regions of mouse 21.6 antibody was built. The model was built on a Silicon Graphics IRIS 4D workstation running under the UNIX operating system and using the molecular modeling package QUANTA (Polygen Corp., USA). The structure of the FRs of mouse 21.6 $V_L$ region was based on the solved structure of human Bence-Jones immunoglobulin REI (Epp et al., *Biochemistry* 14:4943-4952 (1975)). The structure of the FRs of mouse 21.6 $V_H$ region was based on the solved structure of mouse antibody Gloop2. Identical residues in the FRs were retained; non-identical residues were substituted using the facilities within QUANTA. CDR1 and CDR2 of mouse 21.6 $V_L$ region were identified as belonging to canonical structure groups 2 and 1, respectively (Chothia et al., supra). Since CDR1 and CDR2 of REI belong to the same canonical groups, CDR1 and CDR2 of mouse 21.6, $V_L$ region were modeled on the structures of CDR1 and CDR2 of REI. CDR3 of mouse 21.6 $V_L$ region did not appear to correspond to any of the canonical structure groups for CDR3s of $V_L$ regions. A database search revealed, however, that CDR3 in mouse 21.6 $V_L$ region was similar to CDR3 in mouse HyHEL-5 $V_L$ region (Sheriff et al., Proc. Natl. Acad. Sci. USA 84:8075-8079 (1987)). Thus, the CDR3 of mouse 21.6 $V_L$ region was modeled on the structure of CDR3 in mouse HyHEL-5 $V_L$ region. CDR1 and CDR2 of mouse 21.6 $V_H$ region were identified as belonging to canonical structure groups 1 and 2, respectively. CDR1 of mouse 21.6 $V_H$ region was modeled on CDR1 of Gloop2 $V_H$ region which closely resembles members of canonical group 1 for CDR1s of $V_H$ regions. CDR2 of mouse 21.6 $V_H$ region was modeled on CDR2 of mouse HyHEL-5 (Sheriff et al., supra), which is also a member of canonical group 2 for CDR2 for $V_H$ regions. For CDR3s of $V_H$ regions, there are no canonical structures. However, CDR3 in mouse 21.6 $V_H$ region was similar to CDR3 in mouse R19.9 $V_H$ region (Lascombe et al., *Proc. Natl. Acad. Sci. USA* 86:607-611 (1989)) and was modeled on this CDR3 by removing an extra serine residue present at the apex of the CDR3 loop of mouse R19.9 $V_H$ region and annealing and refining the gap. The model was finally subjected to steepest descents and conjugate gradients energy minimization using the CHARMM potential (Brooks et al., *J. Comp. Chem.* 4:187-217 (1983)) as implemented in QUANTA in order to relieve unfavorable atomic contacts and to optimize van der Waals and electrostatic interactions.

A view of the structural model of the mouse 21.6 variable regions is presented in FIG. 5. The model was used to assist in refining the design of the humanized 21.6 antibody variable regions.

Example 5

Design of Reshaped Human 21.6 Variable Regions (1) Selection of Homologous Human Antibodies for Framework Sequence Human variable regions whose FRs showed a high percent identity to those of mouse 21.6 were identified by comparison of amino acid sequences. Tables 4 and 5 compare the mouse 21.6 variable regions to all known mouse variable regions and then to all known human variable regions. The mouse 21.6 $V_L$ region was identified as belonging to mouse kappa $V_L$ region subgroup 5 as defined by Kabat et al., supra. Individual mouse kappa $V_L$ regions were identified that had as much as 93.4% identity to the mouse 21.6 kappa $V_L$ region (38C13'V'CL and PC613'CL). Mouse 21.6 $V_L$ region was most similar to human kappa $V_L$ regions of subgroup 1 as defined by Kabat et al., supra. Individual human kappa $V_L$ regions were identified that had as much as 72.4% identity to the mouse 21.6 kappa $V_L$ region. The framework regions (FRs) from one of the most similar human variable regions, REI, were used in the design of reshaped human 21.6 $V_L$ region. Mouse 21.6 $V_H$ region was identified as belonging to mouse $V_H$ region subgroup 2c as defined by Kabat et al., supra. Individual mouse heavy chain variable regions were identified that have as much as 93.3% identity to the mouse 21.6 $V_H$ region (17.2.25'CL and 87.92.6'CL). Mouse 21.6 $V_H$ region was most similar to human $V_H$ regions of subgroup 1 as defined by Kabat et al., supra. Individual human $V_H$ regions were identified that had as much as 64.7% identity to the mouse 21.6 $V_H$ region. The FRs from one of the most similar human variable regions, 21/28'CL, was used in the design of reshaped human 21.6 $V_H$ region.

(2) Substitution of Amino Acids in Framework Regions (a) Light Chain

The next step in the design process for the reshaped human 21.6 $V_L$ region was to join the CDRs from mouse 21.6 $V_L$ region to the FRs from human REI (Palm et al., supra). In the first version of reshaped human 21.6 $V_L$ region (La), seven changes were made in the human FRs (Table 4, FIG. 6).

At positions 104, 105, and 107 in FR4, amino acids from RE1 were substituted with more typical human J region amino acids from another human kappa light chain (Riechmann et al., Nature 332:323-327 (1988)).

At position 45 in FR2, the lysine normally present in REI was changed to an arginine as found at that position in mouse 21.6 $V_L$ region. The amino acid residue at this position was thought to be important in the supporting the CDR2 loop of the mouse 21.6 $V_L$ region.

At position 49 in FR2, the tyrosine normally present in REI was changed to an histidine as found at that position in mouse 21.6 $V_L$ region. The histidine at this position in mouse 21.6 $V_L$ region was observed in the model to be located in the middle of the binding site and could possibly make direct contact with antigen during antibody-antigen binding.

At position 58 in FR3, the valine normally present in REI was changed to an isoleucine as found at that position in mouse 21.6 $V_L$ region. The amino acid residue at this position was thought to be important in the supporting the CDR2 loop of the mouse 21.6 $V_L$ region.

At position 69 in FR3, the threonine normally present in REI was changed to an arginine as found at that position in mouse 21.6 $V_L$ region. The arginine at this position in mouse 21.6 $V_L$ region was observed in the model to be located adjacent to the CDR1 loop of mouse 21.6 $V_L$ region and could possibly make direct contact with the antigen during antibody-antigen binding.

A second version of reshaped human 21.6 $V_L$ region (termed Lb) was designed containing the same substitutions as above except that no change was made at position 49 in FR2 of REI. (FIG. 6).

(b) Heavy Chain

The next step in the design process for the reshaped human 21.6 $V_H$ region was to join the CDRs from mouse 21.6 $V_H$ region to the FRs from 21/28'CL (Dersimonian et al., J. Immunol. 139:2496-2501 (1987)). In the first version of reshaped human 21.6 V. region (Ha), five changes were made in the human framework regions (Table 5, FIG. 7). The five changes in the human FRs were at positions 27, 28, 29, 30, and 71.

At positions 27, 28, 29, and 30 in FR1, the amino acids present in human 21/28'CL were changed to the amino acids found at those positions in mouse 21.6 $V_H$ region. Although these positions are designated as being within FR1 (Kabat et al., supra), positions 26 to 30 are part of the structural loop that forms the CDR1 loop of the $V_H$ region. It is likely, therefore, that the amino acids at these positions are directly involved in binding to antigen. Indeed, positions 27 to 30 are part of the canonical structure for CDR1 of the $V_H$ region as defined by Chothia et al., supra.

At position 71 in FR3, the arginine present in human 21/28'CL was changed to a alanine as found at that position in mouse 21.6 $V_H$ region. Position 71 is part of the canonical structure for CDR2 of the $V_H$ region as defined by Chothia et al., supra. From the model of the mouse 21.6 variable regions, it appears that the alanine at position 71 is important in supporting the CDR2 loop of the $V_H$ region. A substitution of an arginine for an alanine at this position would very probably disrupt the placing of the CDR2 loop.

A second version (Hb) of reshaped human 21.6 $V_H$ region contains the five changes described above for version Ha were made plus one additional change in FR2.

At position 44 in FR2, the arginine present in human 21/28'CL was changed to a glycine as found at that position in mouse 21.6 $V_H$ region. Based on published information on the packing Of $V_L$-$V_H$ regions and on the model of the mouse 21.6 variable regions, it was thought that the amino acid residue at position 44 might be important in the packing of the $V_L$-$V_H$ regions (Chothia et al., supra) (FIG. 5).

Reshaped human 21.6 V. region version Hc was designed to make the CDR3 loop look more similar to human VCAM-1. Both mouse 21.6 antibody and human VCAM-1 bind to the α4β1 integrin. The CDR3 loop of the $V_H$ region of antibodies is the most diverse of the six CDR loops and is generally the most important single component of the antibody in antibody-antigen interactions (Chothia et al., supra; Hoogenboom & Winter, J. Mol. Biol. 227:381-388 (1992); Barbas et al., Proc. Natl. Acad. Sci. USA 89:4457-4461 (1992)). Some sequence similarity was identified between the CDR3 of mouse 21.6 $V_H$ region and amino acids 86 to 94 of human VCAM-1, particularly, between the YGN (Tyrosine-Glycine-Asparagine) sequence in the CDR3 loop and the FGN (Phenylalanine-Glycine-Asparagine) sequence in VCAM-1. These sequences are thought to be related to the RGD (Arginine-Glycine-Aspartic acid) sequences important in various cell adhesion events (Main et al., Cell 71:671-678 (1992)). Therefore, at position 98 in CDR3, the tyrosine present in mouse 21.6 $V_H$ region was changed to a phenylalanine as found in the sequence of human VCAM-1.

Possible substitution at position 36 in FR2 was also considered. The mouse 21.6 $V_H$ chain contains an unusual cysteine residue at position 36 in FR2. This position in FR2 is usually a tryptophan in related mouse and human sequences (Table 5). Although cysteine residues are often important for conformation of an antibody, the model of the mouse 21.6 variable regions did not indicate that this cysteine residue was involved either directly or indirectly with antigen binding so the tryptophan present in FR2 of human 21/28'CL $V_H$ region was left unsubstituted in all three versions of humanized 21.6 antibody.

Example 6

Construction of Reshaped Human 21.6 Antibodies

Figure 8:
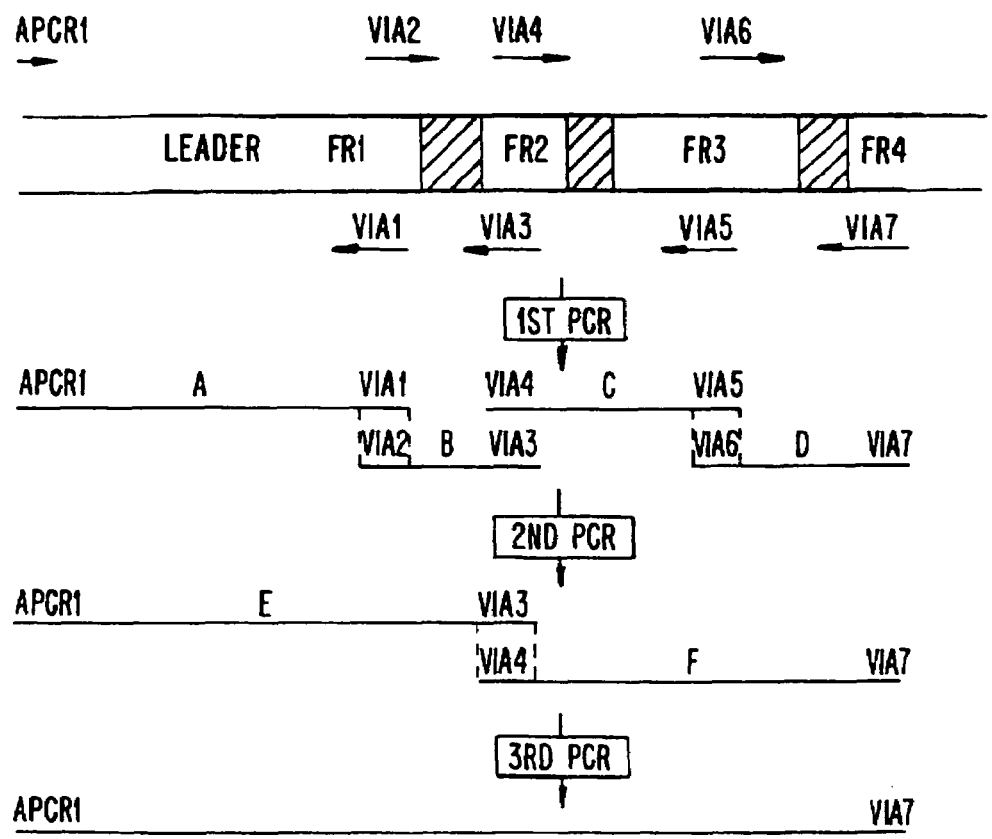
FIG. 8: PCR-based construction of version "a" of reshaped human 21.6 light chain variable region. The dotted lines indicate a complementary sequence of at least 21 bases between the primers.

The first version of reshaped human 21.6 $V_L$ region (resh21.6VLa) was constructed from overlapping PCR fragments essentially as described by Daugherty et al., *Nucleic Acids Res.* 19:2471-2476 (1991). (See FIG. 8). The mouse 21.6 $V_L$ region, adapted as described in Example 2 and inserted into pUC19, was used as a template. Four pairs of primers, APCR1-vla1, vla2-vla3, vla4-vla5, and vla6-vla7 were synthesized (Table 6 and FIG. 8). Adjacent pairs overlapped by at least 21 bases. The APCR1 primer is complementary to the pUC19 vector. The appropriate primer pairs (0.2 μmoles) were combined with 10 ng of template DNA, and 1 unit of AmpliTaq DNA polymerase (Perkin Elmer Cetus) in 50 μl of PCR buffer containing 10 mM Tris-HCl (pH 8.3), 50 mM KCl, 200 μM dNTPs, and 1.5 mM $MgCl_2$. Each reaction was carried out for 25 cycles. After an initial melt at 94° for 5 min, the reactions were cycled at 94° C. for 1 min, 55° C. for 1 min, and 72° C. for 2 min, and finally incubated at 72° C. for a further 10 min. The ramp time between the primer-annealing and extension steps was 2.5 min. The products of the four reactions (A, B, C, and D) from the first round of PCR reactions were phenol-extracted and ethanol-precipitated.

TABLE 6

PCR primers for the construction of reshaped human 21.6 variable regions.

A. Light chain variable region
1. Primers for the synthesis of version "a"

21.6VLa1 (39mer) (SEQ. ID NO:22):
5' GAT GGT GAC TCT ATC TCC TAC AGA TGC AGA CAG TGA GGA 3'

21.6VLa2 (32mer) (SEQ. ID NO:23):
5' CTG TAG GAG ATA GAG TCA CCA TCA CTT GCA AG 3'

21.6VLa3 (39mer) (SEQ. ID NO:24):
5' AGG AGC TTT TCC AGG TGT CTG TTC GTA CCA AGC CAT ATA 3'

21.6VLa4 (41mer) (SEQ. ID NO:25):
5' ACC AAC AGA CAC CTG GAA AAG CTC CTA GGC TGC TCA TAC AT 3'

21.6VLa5 (40mer) (SEQ. ID NO:26):
5' GCA GGC TGC TGA TGG TGA AGT TAT AAT CTC TCC CAG ACC C 3'

21.6VLa6 (42mer) (SEQ. ID NO:27):
5' ACT TTC ACC ATC AGC AGC CTG CAG CCT GAA GAT ATT GCA ACT 3'

21.6VLa7 (59mer) (SEQ. ID NO:28):
5' CCG AGG ATC CAC TCA CGT TTG ATT TCC ACC TTG GTG CCT TGA CCG AAC GTC CAC AGA TT 3'

2. Primers for the synthesis of version "b"
21.6VLb1 (33mer) (SEQ. ID NO:29): changes H-49 to Y-49
5' GGA AAA GCT CCT AGG CTG CTC ATA TAT TAC ACA 3'

21.6VLb2 (38mer (SEQ. ID NO:30)): changes ACC-101 to ACA-101 to destroy an StyI site
5' CCG AGG ATC CAC TCA CGT TTG ATT TCC ACC TTT GTG CC 3'

B. Heavy chain variable region
1. Primers for the synthesis of version "a"

21.6VHa1 (51mer) (SEQ. ID NO:31):
5' AAC CCA GTG TAT ATA GGT GTC TTT AAT GTT GAA ACC GCT AGC TTT ACA GCT 3'

21.6VHa2 (67mer) (SEQ. ID NO:32):
5' AAA GAC ACC TAT ATA CAC TGG GTT AGA CAG GCC CCT GGC CAA AGG CTG GAG TGG ATG GGA AGG ATT G 3'

21.6VHa3 (26mer) (SEQ. ID NO:33):
5' GAC CCG GCC CTG GAA CTT CGG GTC AT 3'

21.6VHa4 (66mer) (SEQ. ID NO:34):
5' GAC CCG AAG TTC CAG GGC CGG GTC ACC ATC ACC GCA GAC ACC TCT GCC AGC ACC GCC TAC ATG GAA 3'

21.6VHa5 (64mer) (SEQ. ID NO:35):
5' CCA TAG CAT AGA CCC CGT AGT TAC CAT AAT ATC CCT CTG GCG CAG TAG T AGA CTG CAG TGT C 3'

TABLE 6-continued

PCR primers for the construction of reshaped
human 21.6 variable regions.

21.6VHa6 (63mer) (SEQ. ID NO:36):
5' GGT AAC TAC GGG GTC TAT GCT ATG GAC TAC TGG GGT CAA GGA ACC CTT GTC
ACC GTC TCC TCA 3'

2. Primer for the synthesis of version "b"

21.6VHb (37mer) (SEQ. ID NO:37): changes R-44 to G-44
5' CCA GGG CCG GGT CAC CAT CAC CAG AGA CAC CTC TGC C 3'

3. Primer for the synthesis of version "c"

21.6VHc (27mer) (SEQ. ID NO:38): changes Y-98 to F-98
5' CAG GCC CCT GGC CAA GGG CTG GAG TGG 3'

C. Both light and heavy chain variable regions
Primers hybridizing to the flanking pUC19 vector DNA APCR1 (17mer (SEQ. ID NO:39), sense primer)
5' TAC GCA AAC CGC CTC TC 3'

APCR4 (18mer (SEQ. ID NO:40), anti-sense primer)
5' GAG TGC ACC ATA TGC GGT 3'

PCR products A and B, and C and D were joined in a second round of PCR reactions. PCR products A and B, and C and D, (50 ng of each) were added to 50 µl PCR reactions (as described above) and amplified through 20 cycles as described above, except that the annealing temperature was raised to 60° C. The products of these reactions were termed E and F. The pairs of PCR primers used were APCR1-vla3 and vla4-vla7, respectively. PCR products E and F were phenol-extracted and ethanol-precipitated and then assembled in a third round of PCR reactions by their own complimentarily in a two step-PCR reaction similar to that described above using APCR1 and vla7 as the terminal primers. The fully assembled fragment representing the entire reshaped human 21.6 $V_L$ region including a leader sequence was digested with HindIII and BamHI and cloned into pUC19 for sequencing. A clone having the correct sequence was designated resh21.6VLa.

The second version of a reshaped human 21.6 $V_L$ region (Lb) was constructed using PCR primers to make minor modifications in the first version of reshaped human 21.6 $V_L$ region (La) by the method of Kamman et al., *Nucl. Acids Res.* 17:5404 (1989). Two sets of primers were synthesized (Table 6). Each PCR reaction was essentially carried out under the same conditions as described above. In a first PCR reaction, mutagenic primer 21.6VLb2 was used to destroy a StyI site (Thr-ACC-97 to Thr-ACA-97) to yield resh21.6VLa2. Then, in a second PCR reaction, mutagenic primer 21.6VLb1 (His-49 to Tyr-49) was used with pUC-resh21.6VLa2 as template DNA. The PCR product was cut with StyI and BamHI and subcloned into pUC-resh21.6VLa2, cleaved with the same restriction enzymes. A clone with the correct sequence was designated pUC-resh21.6VLb.

Figure 9:
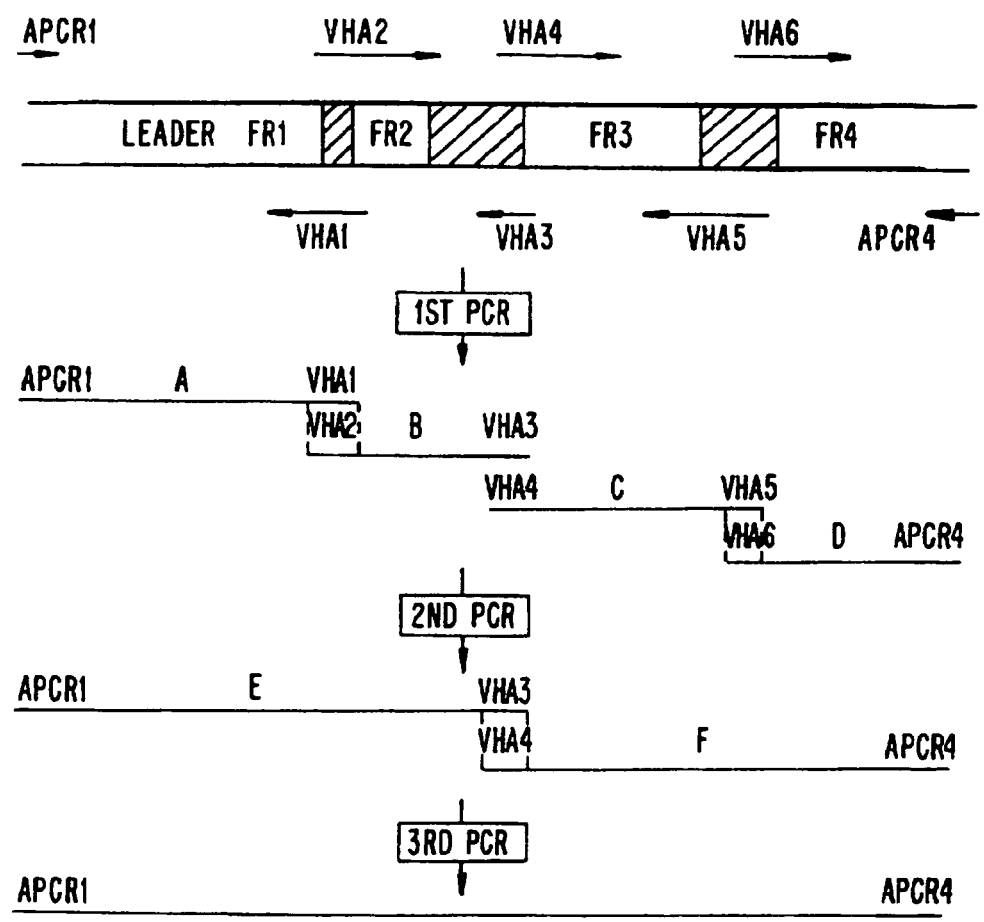
FIG. 9: PCR-based construction of version "a" of reshaped human 21.6 heavy chain variable region.

Version "a" of a reshaped human 21.6 $V_H$ region was constructed using the same PCR methods as described for the construction of version "a" of reshaped human 21.6 $V_L$ region (Table 6 and FIG. 9). The HindIII-BamHI DNA fragments coding for version "g" of reshaped human 425 $V_H$ region (Kettleborough et al., supra) and version "b" of reshaped human AUK12-20 $V_H$ region were subcloned into pUC19 vectors yielding pUC-resh425g and pUC-reshAUK12-20b, respectively. (Version "b" of AUK12-20, was derived by PCR mutagenesis of a fragment $V_H$a425 described by Kettleborough et al., supra, and encodes the amino acid sequence (SEQ. ID NO:41):

QVQLVQSGAEVKKPGASVKVSCKASGYSFT SYYIH WVRQAPGQGLEWV

GYIDPFNGGTSYNQKFKG KVTMTVDTSTNTAYMELSSLRSEDTAVYY

CAR GGN-RFAY WGQGTLVTVSS (spaces separate FR and CDR regions)).

Plasmid pUC-resh425g and pUC-reshAUK12-20b, as well as the pUC vector containing the mouse 21.6 $V_H$ region as modified for use in the construction of the chimeric 21.6 heavy chain (pUC-chim21.6VH), were used as template DNAs in the subsequent PCR reactions. PCR primers were designed and synthesized for the construction of version "a" of reshaped human 21.6 $V_H$ region (Table 6). PCR product A (FIG. 9) was obtained using pUC-reshAUK12-20b as DNA template and APCR1-vha1 as the PCR primer pair. PCR products B and D were obtained using pUC-chim21.6VH as DNA template and vha2-vha3 and vha6-APCR4 as PCR primer pairs, respectively. Finally, PCR product C was obtained using pUC-resh425g as DNA template and vla4-vla5 as the PCR primer pair. The final PCR product was subcloned into pUC19 as an HindIII-BamHI fragment for DNA sequencing. A clone with the correct DNA sequence was designated pUC-resh21.6VHa. The DNA and amino acid sequences of the first version of the reshaped 21.6 variable region are shown in FIG. 10.

The remaining versions of reshaped human 21.6 $V_H$ region were constructed essentially as described above for the construction of version "b" of reshaped human 21.6 $V_L$ region. Two sets of primers were synthesized (Table 6). For the second (Hb) and third (Hc) versions, mutagenic primers 21.6VHb (Arg-44 to Gly-44) and 21.6VHc (Tyr-98 to Phe-98), respectively, were used in PCR reactions with pUC-resh21.6VHa as the template DNA. The PCR products VHb and VHc were cut with restriction enzymes and subcloned into pUC vector pUC-resh21.6VHa as MscI-BamHI and PstI-BamHI fragments, respectively, to yield pUC-resh21.6VHb and pUC-resh21.6VHc.

The first version of a reshaped human 21.6 $V_H$ region (Ha) was constructed in a similar manner to that used for the construction of the first version of reshaped human 21.6 $V_L$ region (La). In this case, however, PCR primers were used with three different template DNAs, mouse 21.6 $V_H$ region as already adapted for expression of chimeric 21.6 heavy chain, humanized 425 $V_H$ region version "g" (Kettleborough et al., supra), and humanized AUK12-20 version "b" $V_H$ region (Table 6, FIG. 9). The DNA and amino acid sequences of the first version of the humanized 21.6 heavy chain variable region are shown in FIG. 11. The second and third versions of a humanized 21.6 $V_H$ region (Hb and Hc) were constructed using PCR primers to make minor modifications in the first version of humanized 21.6 $V_H$ region (Ha) (Table 6).

Example 7

Expression and Analysis of Humanized Antibodies

1. Linkage of Variable Regions to Constant Regions in Expression Vectors

The DNA fragments coding for the chimeric and reshaped 21.6 $V_L$ and $V_H$ regions were subcloned into HCMV vectors designed to express either human kappa light chains or human gamma-1 heavy chains in mammalian cells (see FIG. 3) and Maeda et al., Hum. Antibod. Hybridomas 2:124-134 (1991). Both vectors contain the human cytomegalovirus (HCMV) promoter and enhancer for high level transcription of the immunoglobulin light and heavy chains. The light chain expression vector is exactly as described in Maeda et al., supra, and contains genomic DNA coding for the human kappa constant region (Rabbitts et al., Curr. Top. Microbiol. Immunol. 113:166-171 (1984)). The heavy chain expression vector is essentially as described in Maeda et al., supra, with the exception that the genomic DNA coding for the human gamma-1 constant region was replaced with a cDNA. cDNA coding for human gamma-1 constant region was cloned from a human cell line that secreted a human gamma-1 antibody by PCR. For convenient subcloning into the expression vector, BamHI sites were created at each end of the cDNA. In addition, a splice acceptor site and a 65 bp intron sequence were created at the 5'-end of the cDNA sequence. The BamHI fragment (1176 bp) containing the human gamma-1 cDNA splice acceptor site and intron sequence was substituted for the BamHI fragment (approximately 2.0 kb) in the existing heavy chain vector (Maeda et al., supra). The BamHI site to the 3'-side of the human gamma-1 constant region was then removed with Klenow polymerase.

2. Transfection of Expression Vectors

Expression vectors were introduced into Cos cells by electroporation using the Gene Pulsar apparatus (BioRad). DNA (10 µg of each vector) was added to a 0.8 ml aliquot of 1×10$^7$ cells/ml in PBS. A pulse was delivered at 1,900 volts, 25 µF capacitance. After a 10 min recovery period at ambient temperature, the electroporated cells were added to 8 ml of DMEM (GIBCO) containing 5% heat-inactivated gamma globulin-free fetal calf serum. After 72 h incubation, the medium was collected, centrifuged to remove cellular debris, and stored under sterile conditions at 4° C. for short periods of time, or at −20° C. for longer periods.

3. Purification of Humanized Antibodies

Supernatants from Cos cell transfections were pooled and purified on immobilized Protein A (ImmunoPure IgG Purification Kit, Pierce). The supernatant was sterilized by filtration through a 0.22 µm filter. After mixing with an equal volume of ImmunoPure IgG binding buffer (pH 8.0), the diluted sample was applied to a 1 ml protein A column and allowed to flow completely into the gel. After washing with 15 ml of ImmunoPure IgG binding buffer, the bound antibody was eluted with 5 ml of ImmunoPure IgG elution buffer (pH 2.8), and 1 ml fractions were collected. The pH of the first and second fractions was approximately 8.0. The pH of the third fraction was adjusted to physiological pH by the addition of 100 µl of ImmunoPure binding buffer. The five 1 ml fractions containing the Protein A-purified antibody were then assayed by ELISA to determine the amount of human IgG antibody present in each fraction. Antibody was detected using goat alkaline phosphate-conjugated anti-human IgG (whole molecule, Sigma).

4. Measurement of Binding Affinity

The binding of reshaped human 21.6 antibodies to α4β1 integrin was assayed by ELISA in comparison with mouse and chimeric antibodies. Briefly, L cells transformed to express α4β1 integrin on their cell surface were plated out and grown to confluence in 96-well tissue culture plates. The samples to be tested (either crude supernatants or protein-A-purified) were serially diluted and added to each well. After incubation for 1 h on ice and very gentle washing, goat anti-mouse or anti-human (gamma-chain specific) peroxidase conjugates (Sigma) were added. After a further 1 h incubation on ice and very gentle washing, the substrate (o-phenylenediamine dihydrochloride, Sigma) was added. After incubation for 30 min at room temperature, the reaction was stopped by adding 1 M $H_2SO_4$, and the $A_{490}$ was measured.

Results from analyzing crude supernatants of the two versions of reshaped human 21.6 light chains (La and Lb), in combination with version Ha of reshaped human 21.6 heavy chain, indicated that the La version of reshaped human 21.6 $V_L$ region gave slightly better binding to antigen than version Lb. The La version was therefore used in subsequent experiments. Results from analysis of the crude supernatants of humanized 21.6 heavy chains (Ha and Hb), in combination with version La of humanized 21.6 light chain, showed no significant difference between the two versions (Ha and Hb) of reshaped human $V_H$ regions. Version Ha was selected for use in further experiments because it contained only five changes in the human FRs compared with six changes in the human Hb.

FIG. 12 compares binding of humanized 21.6 antibody (La+Ha) with chimeric 21.6 antibody. The data indicate that the reshaped human 21.6 antibody (La+Ha) bound to antigen as well as, and perhaps slightly better than, the chimeric 21.6 antibody. The chimeric 21.6 antibody is expected to be equivalent to mouse 21.6 antibody in its antigen binding characteristics because it contains the intact mouse 21.6 variable regions. The reshaped human 21.6 antibody (La+Ha) has also been shown to block binding to human α4β1 integrin with an efficiency comparable to the original mouse 21.6 antibody and to the chimeric antibody. It is therefore concluded that reshaped human 21.6 antibody (La+Ha) has a specific binding affinity essentially equal to that of mouse 21.6 antibody. Moreover, because only minor modifications in the human FRs were necessary to recreate the antigen binding site of mouse 21.6 antibody within human variable regions, the reshaped human 21.6 antibody is predicted to behave like an authentic human antibody.

Reshaped human 21.6 antibody containing version La of the reshaped human 21.6 VL region and version Hc of the reshaped human 21.6 VH region was also tested for binding to L cells expressing human α4β1 integrin on their surface in parallel with chimeric 21.6 antibody. The results indicate that reshaped human 21.6 antibody (La+Hc) binds well to antigen. The alteration in the CDR3 of the $V_H$ region did not impair binding to antigen. Indeed, there is some indication that the alteration in the CDR3 may have slightly improved binding to antigen (FIG. 12). Conceivably, the improvement may be more pronounced in a functional blocking assay.

Example 8

Blocking Properties of Mu 21.6 Antibody

Mu 21.6 was compared with another antibody against $\alpha_4$ integrin called L25. L25 is commercially available from Becton Dickinson, and has been reported in the literature to be a good inhibitor of $\alpha_4\beta_1$ integrin adhesive function. As shown in FIG. 13 (Panel A), both Mu 21.6 and L25 completely inhibited $\alpha_4\beta_1$ integrin-dependent adhesion of human monocytic cells to purified VCAM-1 in the absence of $Mn^{+2}$. However, in the presence of $Mn^{+2}$ (1 mM) (one of several activators of $\alpha_4\beta_1$ integrin) L25 was no longer an effective inhibitor. Similar results were observed when $\alpha_4\beta_1$ integrin was activated by other stimuli. The capacity to block activated $\alpha4\beta1$integrin is likely to be of value in treating inflammatory diseases such as multiple sclerosis.

As a further comparison between mu 21.6 and L25, the capacity of antibody to inhibit human T cell adhesion to increasing amounts of VCAM-1 was determined. In this experiment, increasing amounts of VCAM-1 were coated onto plastic wells of a 96 well assay plate, and the ability of the human T cell line, Jurkat (which expresses high levels of $\alpha_4\beta_1$ integrin), to bind to the coated wells was measured. Values on the Y-axis represent the percentage of Jurkat cells originally added to each well that remained bound after washing the well four times (FIG. 13 (Panel B)). This experiment demonstrates that L25 is a good inhibitor of cell adhesion when low levels of VCAM-1 are encountered, but becomes completely ineffective at higher levels of VCAM-1. Mu 21.6, on the other hand, inhibits cell adhesion completely, regardless of the amount of VCAM-1 present. The capacity to block at high concentrations of VCAM-1 is desirable for therapeutic applications because of upregulation of VCAM-1 at sites of inflammation.

Example 9

Efficacy of Humanized 21.6 Antibody in an Animal Model

This example establishes the efficacy of humanized 21.6 antibody in prophylactic and therapeutic treatment of EAE in an animal model simulating multiple sclerosis in humans.

(a) Methods (1) Induction of EAE

The brain and spinal cord were removed from each of five guinea pigs euthanized by $CO_2$ narcosis. The tissue was kept in PBS on wet ice until it was weighed and homogenized at a concentration of 1 gram of tissue per ml PBS. The tissue was completely homogenized using an electric hand-held homogenizer and subsequently mixed with an equal volume of Freund's complete adjuvant (FCA). FCA was made by adding 100 mg of *mycobacterium tuberculosis* H37 RA (DIFCO, 3114-33-8) to 10 ml of Freund's incomplete adjuvant (sigma, F-5506). The mixture was emulsified into the consistency of mayonnaise by passing the solution between two syringes connected by a two way stopcock. Each guinea pig was immunized with 600 μl emulsion divided between three sites of administration.

(2) Scoring Animals for Disease Symptoms

The disease symptoms were assessed by prompting each animal to walk and assigning the animal a score by the following commonly accepted criteria:

| | |
|---|---|
| 0 | No disease |
| 1 | Hind limb weakness |
| 2 | Complete hind limb paralysis |
| 3 | Complete hind limb and some forelimb paralysis |
| 4 | Moribund or dead |

(3) Serum and Tissue Collection

Samples were collected by cardiac puncture from methoxyflurane-anesthetized guinea pigs. About 300-400 μl of blood were collected and placed in microtainer serum separator and allowed to clot for between 20-30 min at room temperature. The tube was then spun for 5 min at room temperature. The serum was drawn off into Eppendorf tubes and stored at −20° C. for subsequent analysis of antibody titers by fluorescence activated cell sorting (FACS).

For hematological analysis, blood was collected into ethylenediaminetetraacetic acid-coated microtainer tubes. A 100 μl aliquot was aspirated into an acridine-coated hematocrit tube. The tube was capped and the blood was mixed with acridine orange by gently inverting the tube 15 times. A float was put into the hematocrit tube and the sample was centrifuged for 5 minutes. The hematocrit tube was placed into a precalibrated Idexx QBC Vet Autoreader designed for quantitative buffey coat analysis. Values were read under the horse calibration system and adjusted to guinea pig equivalents using a predetermined conversion factor.

At the end of the experiment, the guinea pigs were killed by $CO_2$ narcosis and the brains and spinal cords removed. Half of the brain and spinal cord from every guinea pig was snap frozen in 2-methyl butane on dry ice (−20 to −40° C.). This tissue was cut and immunostained with a pan macrophage marker (Serotec MCA-518) and a T-lymphocyte marker (Serotec MCA-751) using the avidin-biotin linking peroxidase assay (Vector Laboratories, Inc., Burlingame, Calif.) and diaminobenzidine as a chromagen. The tissue was scored for cellular infiltration according to the following scoring system:

| | |
|---|---|
| 0 | No infiltrating cells. |
| 0.5 | Very little staining; may be artifactual; usually associated with vessels. |
| 1 | Staining of a few cells (less than 15) usually near a vessel. |
| 2 | Staining of many cells (20-50), usually radiating out from a vessel. |
| 3 | Staining of many cells (>50) scattered throughout the tissue; many cuffed vessels. |

(b) Prophylactic Treatment

This experiment was designed to evaluate the efficacy of humanized 21.6 antibody in delaying the onset of clinical symptoms. Previous data have demonstrated that leukocyte influx into the brain and spinal cord of EAE guinea pigs typically starts between day 7 and day 8. Therefore, antibodies were administered on day 7 and on day 10 post-immunization. To compare mouse and humanized 21.6 antibody, equivalent doses of each of the antibodies (3.0, 0.30 and 0.03 mg/kg) were administered. Preliminary pharmacokinetic studies revealed that saturating blood levels of mouse 21.6 antibody were attained within 24 hours after subcutaneous administration, and remained elevated up to 48 hours.

On day 11, 24 hours after the second dose of antibody, blood samples were drawn from three randomly selected animals in each group. For each treatment group a mean for the number of days for each guinea pig to reach a clinical score of 1 was calculated (Table 7). The mean value for the PBS-treated group in this experiment was 11 days post-immunization (which is typical of previous results). Treatment with the highest dose of humanized and mouse antibody resulted in a significant delay of disease by 4.6 (p=0.000) and 3 (p=0.007) days, respectively. The lower doses of antibody had no effect on the course of disease.

Antibody serum titers were measured by FACS analysis on samples taken 24 hrs after the first injection (Day 14) and at sacrifice (Day 19). Treatment with mouse 21.6 antibody resulted in slightly lower serum antibody titers than treatment with humanized 21.6 antibody (9.1 vs. 12.6 µg/ml). This difference became more profound on Day 19, three days after the second administration, when there was very little detectable serum mouse antibody, while the levels of humanized antibody on Day 19 had dropped below saturating but were still measurable (6.1 µg/ml). These data demonstrate a correlation between plasma levels of antibody and physiologic efficacy and suggest that the effective circulating antibody level is in the range of 10-20 µg/ml in the guinea pig.

TABLE 7

Effect of mouse or humanized 21.6 antibody on time post immunization to reach a clinical score of 1.

| | GROUP | | | | | | |
|---|---|---|---|---|---|---|---|
| | 1 | 2 | 3 | 4 | 5 | 6 | 7 |
| mg/kg | 0.03 M[#] | 3.0 H[@] | 3.0 H | 3.0 M | 0.03 H | PBS | 0.3 M |
| | 8 | 9 | 13 | 10 | 8 | 9 | 9 |
| | 9 | 10 | 15 | 12 | 10 | 9 | 9 |
| | 9 | 10 | 15 | 14 | 10 | 11 | 11 |
| | 9 | 11 | 16 | 14 | 11 | 11 | 12 |
| | 11 | 11 | 16 | 14 | 12 | 11 | 12 |
| | 12 | 11 | 16 | 15 | 12 | 12 | 13 |
| | 12 | 12 | 17 | 15 | 12 | 12 | 13 |
| | | | 13 | 17 | 18 | 12 | 13 |
| Mean ± SD | 10.0 ± 1.6 | 10.9 ± 1.2 | **15.6 ± 1.3 | *14.0 ± 2.3 | 10.9 ± 1.5 | 11.0 ± 1.4 | 11.6 ± 1.4 |

[@]H denotes humanized antibody;
[#]M denotes mouse.
**p = 0.000 and
*p = 0.007, as compared to PBS.

Figure 14:
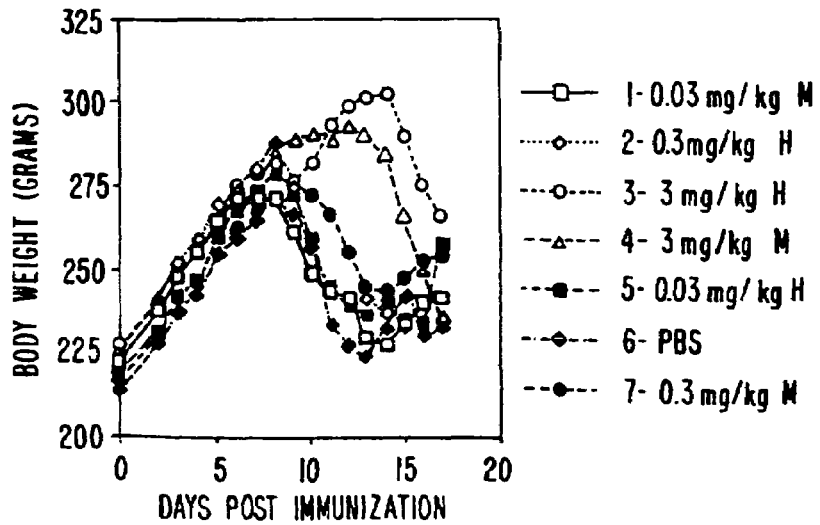
FIG. 14: Delay of weight loss in animals treated with mouse or human 21.6 antibody.

Daily body weights of the guinea pig reflected a similar effect of the high doses of humanized and mouse antibody. (FIG. 14). Animals in these treatment groups steadily gained weight. Guinea pigs in all other treatment groups lost weight starting from just before the day of onset of disease.

Serum titers of antibody were measured in three randomly selected animals from each group by cardiac puncture on day 11, roughly 24 hr after the second treatment. Efficacy of the antibodies to delay disease correlated tightly with serum levels. About 20 µg/ml serum antibody was present in the circulation of all animals injected with the highest dose of both humanized and mouse antibodies. This concentration is of the same order of magnitude as the concentration of 21.6 antibody required to saturate alpha-4 integrin sites in vitro. In contrast, animals from all other groups had little to no detectable serum antibody.

(c) Reversal of On-Going Disease

Figure 15:
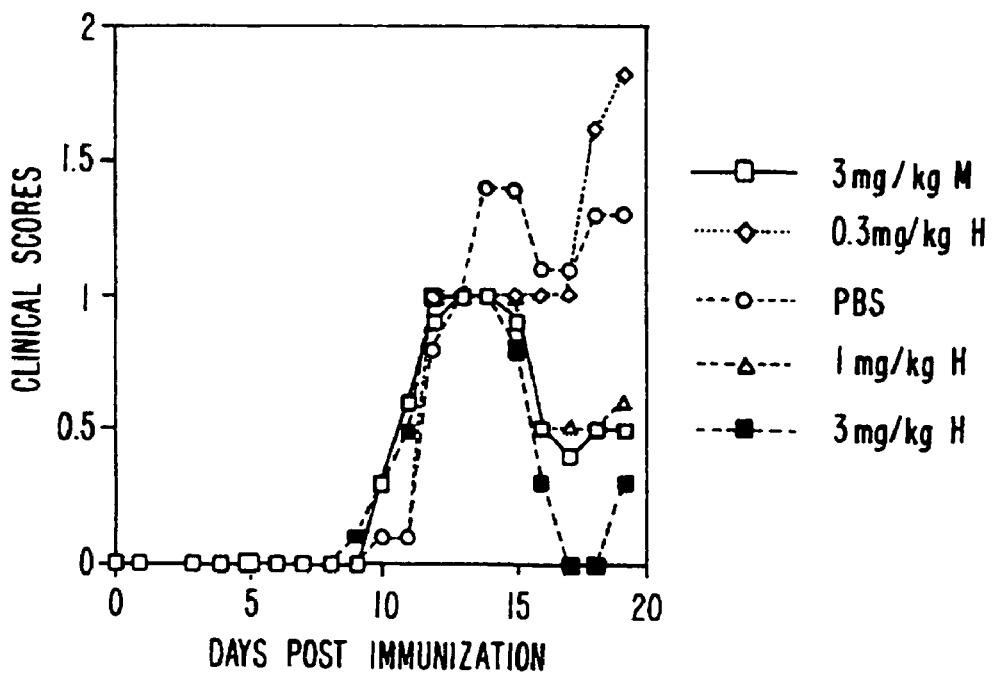
FIG. 15: Reversal of clinical symptoms in animals treated with mouse or human 21.6 antibody.
Figure 16:
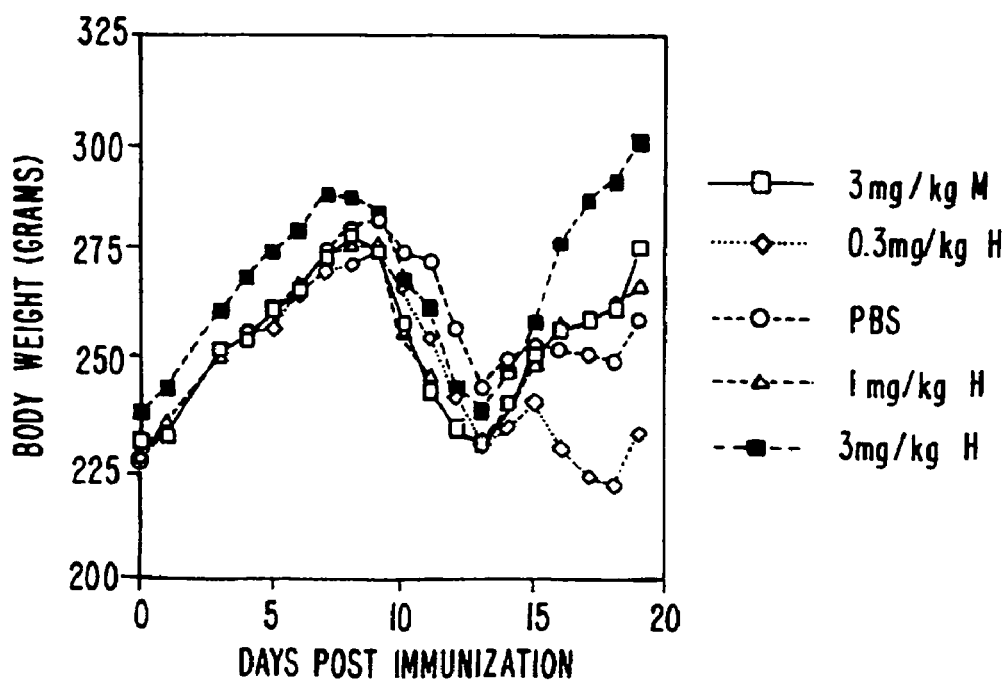
FIG. 16: Reversal of weight loss in animals treated with mouse or human 21.6 antibody.

About 60 guinea pigs were immunized and allowed to develop clinical symptoms of EAE. On day 13, all guinea pigs that attained a clinical score of 1 were randomly assigned to a treatment group. FIG. 15 shows that animals treated with 3 mg/kg humanized antibody began to recover hind limb function within 48 hr of treatment. On Days 17 and 18, one and two days after the second dose, all eight animals were disease free. ANOVA of the area under the curve values for each treatment group revealed that only the 3 mg/kg humanized antibody treated group value was statistically lower than the PBS control group (p=0.042). These animals progressively gained weight within 24 hrs after the first administration until the experiment was terminated on Day 19 (FIG. 16).

Leukocyte infiltration onto brain and spinal cord was evaluated in tissue from animals killed on Day 19. Table 8 shows significant differences in the degree of infiltration as a function of antibody treatment. The reduction in T cell infiltration into brain and spinal cord and macrophage infiltration into spinal cord was significant after treatment with 3 mg/kg. Lower doses tended to reduce infiltration, but did not reach significance. There was no significant difference in cellular infiltrate of macrophages into the spinal cord at any dose. Since the immunohistochemical technique used to evaluate macrophages does not distinguish resident from invading cells, the lack of effect on macrophages likely represents the sustained presence of resident macrophages and microglia.

The reduction in T-cells and monocytes in brain tissue by administration of the antibody after establishment of the disease suggests that cell trafficking is not a cumulative process, but a dynamic movement of cells into and out of CNS tissue. Importantly, the data suggest that interruption of the entry of leukocytes into parenchymal tissue allows the CNS to rid itself of the invading pathological element.

TABLE 8

Significant differences in T-cell and macrophage infiltration into brain and spinal cord on Day 129.

| | BRAIN | | SPINAL CORD | |
|---|---|---|---|---|
| GROUP PBS | T-CELLS | MACRO-PHAGES | T-CELLS | MACRO-PHAGES |
| 3 mg/kg @ H | p = 0.001 | p = 0.005 | p = 0.007 | NS |
| 3 mg/kg # M | p = 0.001 | p = 0.005 | p = 0.008 | NS |

TABLE 8-continued

Significant differences in T-cell and macrophage infiltration into brain and spinal cord on Day 129.

| | BRAIN | | SPINAL CORD | |
|---|---|---|---|---|
| GROUP PBS | T-CELLS | MACRO-PHAGES | T-CELLS | MACRO-PHAGES |
| 1 mg/kg H | NS | NS | NS | NS |
| 0.3 mg/kg H | NS | NS | NS | NS |

NS = not significant.

Hematology data revealed that treatment with mouse or humanized 21.6 antibody caused no difference in whole white blood cell counts, mononuclear and granulocyte number or in red blood cell count. The high dose of mouse or humanized antibody resulted in a significant increase in platelet counts as compared to PBS treated animals (Table 9). In normal guinea pig platelet counts are 755±103 cells/ml, about double that of PBS-treated EAE animals. Thus, treatment with doses of mouse and humanized antibody that effectively reversed disease, also restored platelet count to normal.

TABLE 9

Effect of antibody treatment on platelet count in EAE animals.

| TREATMENT | PLATELETS × $10^{-6}$ CELLS/ML |
|---|---|
| ++Non EAE guinea pigs | 755 ± 103 (9) |
| PBS | 373.7 ± 167.5 (7) |
| 3 mg/kg @ H | 622.2 ± 97.0 (6)** |
| 3 mg/kg # M | 587.5 ± 57.8 (6) |
| 1 mg/kg H | 578.3 ± 123.2 (6) |
| 0.3 mg/kg H | 492.5 ± 168.6 (6) |

++Platelet counts in non-EAE guinea pigs were determined in a separate experiment.
*p = 0.05 vs PBS.

In conclusion, both humanized and mouse 21.6 antibodies are effective in delaying and reversing clinical symptoms in an animal model simulating multiple sclerosis in humans. The humanized antibody is more effective than the same dosage of mouse antibody in reversing symptoms.

Although the foregoing invention has been described in detail for purposes of clarity of understanding, it will be obvious that certain modifications may be practiced within the scope of the appended claims. All publications and patent documents cited above are hereby incorporated by reference in their entirety for all purposes to the same extent as if each were so individually denoted.

TABLE 4

Alignment of amino acid sequences leading to the design of reshaped human 21.6 light chain variable regions.

| Kabat | # | FR or CDR | mouse 21.6 | mouse kappa 5 (SEQ. ID NO: 42) | human kappa 1 (SEQ. ID NO: 43) | human RE1 | RH $V_L$ 21.6 | Comment |
|---|---|---|---|---|---|---|---|---|
| 1 | 1 | FR1 | D | D | D | D | D | |
| 2 | 2 | | I | I | I | I | I* | |
| 3 | 3 | | Q | Q | Q | Q | Q | |
| 4 | 4 | | M | M | M | M | M | |
| 5 | 5 | | T | T | T | T | T | |
| 6 | 6 | | Q | Q | Q | Q | Q | |
| 7 | 7 | | S | S | S | S | S | |
| 8 | 8 | | P | P | P | P | P | |
| 9 | 9 | | S | S | S | S | S | |
| 10 | 10 | | S | S | S | S | S | |
| 11 | 11 | | L | L | L | L | L | |
| 12 | 12 | | S | S | S | S | S | |
| 13 | 13 | | A | A | A | A | A | |
| 14 | 14 | | S | S | S | S | S | |
| 15 | 15 | | L | L | V | V | V | |
| 16 | 16 | | G | G | G | G | G | |
| 17 | 17 | | G | D | D | D | D | |
| 18 | 18 | | K | R | R | R | R | |
| 19 | 19 | | V | V | V | V | V | |
| 20 | 20 | | T | T | T | T | T | |
| 21 | 21 | | I | I | I | I | I | |
| 22 | 22 | | T | T | T | T | T | |
| 23 | 23 | FR1 | C | C | C | C | C | |
| 24 | 24 | CDR1 | K | R | R | Q | K | |
| 25 | 25 | | T | A | A | A | T* | |
| 26 | 26 | | S | S | S | S | S* | |
| 27 | 27 | | Q | Q | Q | Q | Q* | |
| 27A | | | — | D | S | — | — | |
| 27B | | | — | — | L | — | — | |
| 27C | | | — | — | V | — | — | |
| 27D | | | — | — | X | — | — | |
| 27E | | | — | — | X | — | — | |
| 27F | | | — | — | — | — | — | |
| 28 | 28 | | D | D | S | D | D* | |

TABLE 4-continued

Alignment of amino acid sequences leading to the design of reshaped human 21.6 light chain variable regions.

| Kabat | # | FR or CDR | mouse 21.6 | mouse kappa 5 (SEQ. ID NO: 42) | human kappa 1 (SEQ. ID NO: 43) | human RE1 | RH V$_L$ 21.6 | Comment |
|---|---|---|---|---|---|---|---|---|
| 29 | 29 |  | I | I | I | I | I* |  |
| 30 | 30 |  | N | S | S | I | N* |  |
| 31 | 31 |  | K | N | N | K | K* |  |
| 32 | 32 |  | Y | Y | Y | Y | Y* |  |
| 33 | 33 |  | M | L | L | L | M* |  |
| 34 | 34 | CDR1 | A | N | A | N | A |  |
| 35 | 35 | FR2 | W | W | W | W | W |  |
| 36 | 36 |  | Y | Y | Y | Y | Y |  |
| 37 | 37 |  | Q | Q | Q | Q | Q |  |
| 38 | 38 |  | H | Q | Q | Q | Q |  |
| 39 | 39 |  | K | K | K | T | T | K in CAMPATH-1H |
| 40 | 40 |  | P | P | P | P | P |  |
| 41 | 41 |  | G | G | G | G | G |  |
| 42 | 42 |  | K | G | K | K | K |  |
| 43 | 43 |  | R | S | A | A | A | consider R in other versions |
| 44 | 44 |  | P | P | P | P | P |  |
| 45 | 45 |  | R | K | K | K | R | supports L2 loop, consider K in other versions |
| 46 | 46 |  | L | L | L | L | L |  |
| 47 | 47 |  | L | L | L | L | L |  |
| 48 | 48 |  | I | I | I | I | I* |  |
| 49 | 49 | FR2 | H | Y | Y | Y | H | in middle of binding site, potential to interact with antigen, consider Y in other versions |
| 50 | 50 | CDR2 | Y | Y | A | E | Y* |  |
| 51 | 51 |  | T | A | A | A | T* |  |
| 52 | 52 |  | S | S | S | S | S* |  |
| 53 | 53 |  | A | R | S | N | A |  |
| 54 | 54 |  | L | L | L | L | L |  |
| 55 | 55 |  | Q | H | E | Q | Q |  |
| 56 | 56 | CDR2 | P | S | S | A | P |  |
| 57 | 57 | FR3 | G | G | G | G | G |  |
| 58 | 58 |  | I | V | V | V | I | may be supporting L2, consider V in other versions |
| 59 | 59 |  | P | P | P | P | P |  |
| 60 | 60 |  | S | S | S | S | S |  |
| 61 | 61 |  | R | R | R | R | R |  |
| 62 | 62 |  | F | F | F | F | F |  |
| 63 | 63 |  | S | S | S | S | S |  |
| 64 | 64 |  | G | G | G | G | G* |  |
| 65 | 65 |  | S | S | S | S | S |  |
| 66 | 66 |  | G | G | G | G | G |  |
| 67 | 67 |  | S | S | S | S | S |  |
| 68 | 68 |  | G | G | G | G | G |  |
| 69 | 69 |  | R | T | T | T | R | adjacent to L1, on the surface near the binding site |
| 70 | 70 |  | D | D | D | D | D |  |
| 71 | 71 |  | Y | Y | F | Y | Y* | F in CAMPATH-1H |
| 72 | 72 |  | S | S | T | T | T |  |
| 73 | 73 |  | F | L | L | F | F |  |
| 74 | 74 |  | N | T | T | T | T |  |

TABLE 4-continued

Alignment of amino acid sequences leading to the design of reshaped human 21.6 light chain variable regions.

| Kabat | # | FR or CDR | mouse 21.6 | mouse kappa 5 (SEQ. ID NO: 42) | human kappa 1 (SEQ. ID NO: 43) | human REI | RH V$_L$ 21.6 | Comment |
|---|---|---|---|---|---|---|---|---|
| 75 | 75 | | I | I | I | I | I | |
| 76 | 76 | | S | S | S | S | S | |
| 77 | 77 | | N | N | S | S | S | |
| 78 | 78 | | L | L | L | L | L | |
| 79 | 79 | | E | E | Q | Q | Q | |
| 80 | 80 | | P | Q | P | P | P | |
| 81 | 81 | | E | E | E | E | E | |
| 82 | 82 | | D | D | D | D | D | |
| 83 | 83 | | I | I | F | I | I | |
| 84 | 84 | | A | A | A | A | A | |
| 85 | 85 | | T | T | T | T | T | |
| 86 | 86 | | Y | Y | Y | Y | Y | |
| 87 | 87 | | Y | F | Y | Y | Y | |
| 88 | 88 | FR3 | C | C | C | C | C | |
| 89 | 89 | CDR3 | L | Q | Q | Q | L | |
| 90 | 90 | | Q | Q | Q | Q | Q* | |
| 91 | 91 | | Y | G | Y | Y | Y* | |
| 92 | 92 | | D | N | N | Q | D* | |
| 93 | 93 | | N | T | S | S | N* | |
| 94 | 94 | | L | L | L | L | L* | |
| 95 | | | — | P | P | P | — | |
| 95A | | | — | P | E | — | — | |
| 95B | | | — | — | — | — | — | |
| 95C | | | — | — | — | — | — | |
| 95D | | | — | — | — | — | — | |
| 95E | | | — | — | — | — | — | |
| 95F | | | — | — | — | — | — | |
| 96 | 95 | | W | R | W | Y | W* | |
| 97 | 96 | CDR3 | T | T | T | T | T | |
| 98 | 97 | FR4 | F | F | F | F | F | |
| 99 | 98 | | G | G | G | G | G | |
| 100 | 99 | | G | G | Q | Q | Q | |
| 101 | 100 | | G | G | G | G | G | |
| 102 | 101 | | T | T | T | T | T | |
| 103 | 102 | | K | K | K | K | K | |
| 104 | 103 | | L | L | V | L | <u>V</u> | as in CAMPATH-1H |
| 105 | 104 | | E | E | E | Q | <u>E</u> | as in CAMPATH-1H |
| 106 | 105 | | I | I | I | I | I | |
| 106A | | | — | — | — | — | — | |
| 107 | 106 | FR4 | K | K | K | T | <u>K</u> | as in CAMPATH-1H |

Legend:
(Kabat) numbering according to Kabat et al., supra;
(#) sequential numbering as used in the molecular modelling;
(mouse 21.6) amino acid sequence of the V$_L$ region from mouse 21.6 antibody;
(mouse kappa 5) consensus sequence of mouse kappa V$_L$ regions from subgroup 5 (Kabat et al., supra);
(human kappa 1) consensus sequence of human V$_L$ regions from subgroup 1 (Kabat et al., supra);
(human REI) amino acid sequence of a human V$_L$ region (Palm et al. (1975), supra);
(RH V$_L$ 21.6) amino acid sequence of version L1 of reshaped human 21.6 V$_L$ region;
*residues that are part of the canonical structures for the CDR loops (Chothia et al., supra);
(underlined) residues in the human FRs where the amino acid residue was changed.

TABLE 5

Alignment of amino acid sequences leading to the design of reshaped human 21.6 heavy chain variable regions.

| Kabat | # | FR or CDR | mouse 21.6 | mouse 2c (SEQ. ID NO: 44) | human 1 (SEQ. ID NO: 45) | human 21/28'CL | RH V$_H$ 21.6 | Comment |
|---|---|---|---|---|---|---|---|---|
| 1 | 1 | FR1 | E | E | Q | Q | Q | |
| 2 | 2 |  | V | V | V | V | V | |
| 3 | 3 |  | Q | Q | Q | Q | Q | |
| 4 | 4 |  | L | L | L | L | L | |
| 5 | 5 |  | Q | Q | V | V | V | |
| 6 | 6 |  | Q | Q | Q | Q | Q | |
| 7 | 7 |  | S | S | S | S | S | |
| 8 | 8 |  | G | G | G | G | G | |
| 9 | 9 |  | A | A | A | A | A | |
| 10 | 10 |  | E | E | E | E | E | |
| 11 | 11 |  | L | L | V | V | V | |
| 12 | 12 |  | V | V | K | K | K | |
| 13 | 13 |  | K | K | K | K | K | |
| 14 | 14 |  | P | P | P | P | P | |
| 15 | 15 |  | G | G | G | G | G | |
| 16 | 16 |  | A | A | A | A | A | |
| 17 | 17 |  | S | S | S | S | S | |
| 18 | 18 |  | V | V | V | V | V | |
| 19 | 19 |  | K | K | K | K | K | |
| 20 | 20 |  | L | L | V | V | V | |
| 21 | 21 |  | S | S | S | S | S | |
| 22 | 22 |  | C | C | C | C | C | |
| 23 | 23 |  | T | T | K | K | K | |
| 24 | 24 |  | A | A | A | A | A | |
| 25 | 25 |  | S | S | S | S | S | |
| 26 | 26 |  | G | G | G | G | G* | |
| 27 | 27 |  | F | F | Y | Y | F* | H1 canonical structure, consider Y in other versions |
| 28 | 28 |  | N | N | T | T | N* | H1 canonical structure, on the surface |
| 29 | 29 |  | I | I | F | F | I* | H1 canonical structure, consider F in other versions |
| 30 | 30 | FR1 | K | K | T | T | K* | H1 canonical structure, on the surface |
| 31 | 31 | CDR1 | D | D | S | S | D* | |
| 32 | 32 |  | T | T | Y | Y | T* | |
| 33 | 33 |  | Y | Y | A | A | Y | |
| 34 | 34 |  | I | M | I | M | I* | |
| 35 | 35 |  | H | H | S | H | H | |
| 35A |  |  | — | — | — | — | — | |
| 35B |  | CDR1 | — | — | — | — | — | |
| 36 | 36 | FR2 | C | W | W | W | W | buried residue, no obvious special role for C |
| 37 | 37 |  | V | V | V | V | V | |
| 38 | 38 |  | K | K | R | R | R | |
| 39 | 39 |  | Q | Q | Q | Q | Q | |
| 40 | 40 |  | R | R | A | A | A | |
| 41 | 41 |  | P | P | P | P | P | |
| 42 | 42 |  | E | E | G | G | G | |
| 43 | 43 |  | Q | Q | Q | Q | Q | |
| 44 | 44 |  | G | G | G | R | R | V$_L$ - V$_H$ packing, consider |

TABLE 5-continued

Alignment of amino acid sequences leading to the design of reshaped human 21.6 heavy chain variable regions.

| Kabat | # | FR or CDR | mouse 21.6 | mouse 2c (SEQ. ID NO: 44) | human 1 (SEQ. ID NO: 45) | human 21/28'CL | RH V$_H$ 21.6 | Comment |
|---|---|---|---|---|---|---|---|---|
| | | | | | | | | G in other versions |
| 45 | 45 | | L | L | L | L | L | |
| 46 | 46 | | E | E | E | E | E | |
| 47 | 47 | | W | W | W | W | W | |
| 48 | 48 | | I | I | M | M | M | |
| 49 | 49 | FR2 | G | G | G | G | G | |
| 50 | 50 | CDR2 | R | R | W | W | R | |
| 51 | 51 | | I | I | I | I | I | |
| 52 | 52 | | D | D | N | N | D | |
| 52A | 53 | | P | P | P | A | P* | |
| 52B | | | — | — | Y | — | — | |
| 52C | | | — | — | — | — | — | |
| 53 | 54 | | A | A | G | G | A* | |
| 54 | 55 | | N | N | N | N | N* | |
| 55 | 56 | | G | G | G | G | G* | |
| 56 | 57 | | Y | N | D | N | Y | |
| 57 | 58 | | T | T | T | T | T | |
| 58 | 59 | | K | K | N | K | K | |
| 59 | 60 | | Y | Y | Y | Y | Y | |
| 60 | 61 | | D | D | A | S | D | |
| 61 | 62 | | P | P | Q | Q | P | |
| 62 | 63 | | K | K | K | K | K | |
| 63 | 64 | | F | F | F | F | F | |
| 64 | 65 | | Q | Q | Q | Q | Q | |
| 65 | 66 | CDR2 | G | G | G | G | G | |
| 66 | 67 | FR3 | K | K | R | R | R | |
| 67 | 68 | | A | A | V | V | V | |
| 68 | 69 | | T | T | T | T | T | |
| 69 | 70 | | I | I | I | I | I | |
| 70 | 71 | | T | T | T | T | T | |
| 71 | 72 | | A | A | A | R | A* | H2 canonical structure, supporting H2 |
| 72 | 73 | | D | D | D | D | D | |
| 73 | 74 | | T | T | T | T | T | |
| 74 | 75 | | S | S | S | S | S | |
| 75 | 76 | | S | S | T | A | A | |
| 76 | 77 | | N | N | S | S | S | |
| 77 | 78 | | T | T | T | T | T | |
| 78 | 70 | | A | A | A | A | A | |
| 79 | 80 | | Y | Y | Y | Y | Y | |
| 80 | 81 | | L | L | M | M | M | |
| 81 | 82 | | Q | Q | E | E | E | |
| 82 | 83 | | L | L | L | L | L | |
| 82A | 84 | | S | S | S | S | S | |
| 82B | 85 | | S | S | S | S | S | |
| 82C | 86 | | L | L | L | L | L | |
| 83 | 87 | | T | T | R | R | R | |
| 84 | 88 | | S | S | S | S | S | |
| 85 | 89 | | E | E | E | E | E | |
| 86 | 90 | | D | D | D | D | D | |
| 87 | 91 | | T | T | T | T | T | |
| 88 | 92 | | A | A | A | A | A | |
| 89 | 93 | | V | V | V | V | V | |
| 90 | 94 | | Y | Y | Y | Y | Y | |
| 91 | 95 | | F | Y | Y | Y | Y | |
| 92 | 96 | | C | C | C | C | C | |
| 93 | 97 | | A | A | A | A | A | |
| 94 | 98 | FR3 | R | R | R | R | R* | |
| 95 | 99 | CDR3 | E | G | A | G | E | |
| 96 | 100 | | G | Y | P | G | G | |
| 97 | 101 | | Y | Y | G | Y | Y | |
| 98 | 102 | | Y | Y | Y | Y | Y | |
| 99 | 103 | | G | Y | G | G | G | |
| 100 | 104 | | N | D | S | S | N | |
| 100A | 105 | | Y | S | G | G | Y | |
| 100B | 106 | | G | X | G | S | G | |
| 100C | 107 | | V | V | G | — | V | |
| 100D | 108 | | Y | G | C | — | Y | |

TABLE 5-continued

Alignment of amino acid sequences leading to the design of reshaped human 21.6 heavy chain variable regions.

| Kabat | # | FR or CDR | mouse 21.6 | mouse 2c (SEQ. ID NO: 44) | human 1 (SEQ. ID NO: 45) | human 21/28'CL | RH V$_H$ 21.6 | Comment |
|---|---|---|---|---|---|---|---|---|
| 100E | 109 | | A | Y | Y | — | A | |
| 100F | 110 | | M | Y | R | — | M | |
| 100G | | | — | A | G | — | — | |
| 100H | | | — | M | D | — | — | |
| 100I | | | — | — | Y | — | — | |
| 100J | | | — | — | X | — | — | |
| 100K | | | — | — | F | — | — | |
| 101 | 111 | | D | D | D | N | D | |
| 102 | 112 | CDR3 | Y | Y | Y | Y | Y | |
| 103 | 113 | FR4 | W | W | W | W | W | |
| 104 | 114 | | G | G | G | G | G | |
| 105 | 115 | | Q | Q | Q | Q | Q | |
| 106 | 116 | | G | G | G | G | G | |
| 107 | 117 | | T | T | T | T | T | |
| 108 | 118 | | S | X | L | L | L | |
| 109 | 119 | | V | V | V | V | V | |
| 110 | 120 | | T | T | T | T | T | |
| 111 | 121 | | V | V | V | V | V | |
| 112 | 122 | | S | S | S | S | S | |
| 113 | 123 | FR4 | S | S | S | S | S | |

Legend:
(Kabat) numbering according to Kabat et al., supra;
(#) sequential numbering as used in the molecular modelling;
(mouse 21.6) amino acid sequence of the V$_H$ region from mouse 21.6 antibody;
(mouse 2c) consensus sequence of mouse V$_H$ regions from subgroup 2c (Kabat et al., supra);
(human 1) consensus sequence of human V$_H$ regions from subgroup 1 (Kabat et al., supra);
(human 21/28'CL) amino acid sequence of a human V$_H$ region (Dersimonian et al. (1987), supra,);
(RH V6$_H$ 21.6) amino acid sequence of version H1 of reshaped human 21.6 V$_H$ region;
*residues that are part of the canonical structures for the CDR loops (Chothia et al., supra);
(underlined) residues in the human FRs where the amino acid residue was changed.

```

What is claimed is:

1. A humanized immunoglobulin or antigen-binding fragment of a humanized immunoglobulin, comprising:
   (a) a light chain variable region comprising complementarity determining regions CDR1, CDR2, and CDR3 of a mouse 21.6 immunoglobulin light chain variable region (SEQ ID NO:2) in a variable region framework of a human kappa light chain variable region,
   wherein at least one amino acid position in said variable region framework selected from the group consisting of L45, L49, L58, and L69, designated according to the Kabat numbering convention, is substituted with the amino acid present in the equivalent position of said mouse 21.6 immunoglobulin light chain variable region,
   and wherein the amino acid at one or more positions selected from the group consisting of L104, L105, and L107, designated according to the Kabat numbering convention, may be substituted with an amino acid present in the corresponding position in a different human immunoglobulin light chain framework; and,
   (b) a heavy chain variable region comprising complementarity determining regions CDR1, CDR2 and CDR3 of a mouse 21.6 immunoglobulin heavy chain variable region (SEQ ID NO:4) in a variable region framework of a human heavy chain variable region,
   wherein at least one framework amino acid position selected from the group consisting of: H27, H28, H29, H30, H44 and H71, designated according to the Kabat numbering convention, is substituted with the amino acid from the corresponding position in a mouse 21.6 heavy chain variable region sequence
   and further wherein positions H36 and H98, designated according to the Kabat numbering convention, may be substituted with a human heavy chain framework residue,
   and wherein the humanized immunoglobulin or anticien-binding fragment of a humanized immunoglobulin has an antigenic specificity for alpha-4 integrin or VLA-4.

* * * * *

                       SEQUENCE LISTING (1) GENERAL INFORMATION:

(iii) NUMBER OF SEQUENCES:  45

(2) INFORMATION FOR SEQ ID NO:1:

(i) SEQUENCE CHARACTERISTICS:
        (A) LENGTH: 483 base pairs
        (B) TYPE: nucleic acid
        (C) STRANDEDNESS: double
        (D) TOPOLOGY: linear (ii) MOLECULE TYPE: cDNA (ix) FEATURE:
         (A) NAME/KEY: CDS
         (B) LOCATION: 53..430

(xi) SEQUENCE DESCRIPTION: SEQ ID NO:1:

ATGAGGGCCC CTGCTCAGAT TTTTGGATTC TTGGTCAGGA GACGTTGTAG AA ATG          55
                                                            Met
                                                            1

AGA CCG TCT ATT CAG TTC CTG GGG CTC TTG TTG TTC TGG CTT CAT GGT      103
Arg Pro Ser Ile Gln Phe Leu Gly Leu Leu Leu Phe Trp Leu His Gly
            5                   10                  15

GCT CAG TGT GAC ATC CAG ATG ACA CAG TCT CCA TCC TCA CTG TCT GCA      151
Ala Gln Cys Asp Ile Gln Met Thr Gln Ser Pro Ser Ser Leu Ser Ala
        20                  25                  30
```

```
TCT CTG GGA GGC AAA GTC ACC ATC ACT TGC AAG ACA AGC CAA GAC ATT        199
Ser Leu Gly Gly Lys Val Thr Ile Thr Cys Lys Thr Ser Gln Asp Ile
 35              40                  45

AAC AAG TAT ATG GCT TGG TAC CAA CAC AAG CCT GGA AAA CGT CCT AGG        247
Asn Lys Tyr Met Ala Trp Tyr Gln His Lys Pro Gly Lys Arg Pro Arg
 50              55                  60                  65

CTG CTC ATA CAT TAC ACA TCT GCA TTA CAG CCA GGC ATC CCA TCA AGG        295
Leu Leu Ile His Tyr Thr Ser Ala Leu Gln Pro Gly Ile Pro Ser Arg
                 70                  75                  80

TTC AGT GGA AGT GGG TCT GGG AGA GAT TAT TCC TTC AAC ATC AGC AAC        343
Phe Ser Gly Ser Gly Ser Gly Arg Asp Tyr Ser Phe Asn Ile Ser Asn
                 85                  90                  95

CTG GAG CCT GAA GAT ATT GCA ACT TAT TAT TGT CTA CAG TAT GAT AAT        391
Leu Glu Pro Glu Asp Ile Ala Thr Tyr Tyr Cys Leu Gln Tyr Asp Asn
                100                 105                 110

CTG TGG ACG TTC GGT GGA GGC ACC AAG CTG GAA ATC AAA CGGGCTGATG         440
Leu Trp Thr Phe Gly Gly Gly Thr Lys Leu Glu Ile Lys
                115                 120                 125

CTGCACCAAC TGTATCCATC TTCCCACCAT CCACCCGGGA TCC                        483

(2) INFORMATION FOR SEQ ID NO:2:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:2:

Met Arg Pro Ser Ile Gln Phe Leu Gly Leu Leu Leu Phe Trp Leu His
 1               5                  10                  15

Gly Ala Gln Cys Asp Ile Gln Met Thr Gln Ser Pro Ser Ser Leu Ser
                 20                  25                  30

Ala Ser Leu Gly Gly Lys Val Thr Ile Thr Cys Lys Thr Ser Gln Asp
             35                  40                  45

Ile Asn Lys Tyr Met Ala Trp Tyr Gln His Lys Pro Gly Lys Arg Pro
 50                  55                  60

Arg Leu Leu Ile His Tyr Thr Ser Ala Leu Gln Pro Gly Ile Pro Ser
 65              70                  75                  80

Arg Phe Ser Gly Ser Gly Ser Gly Arg Asp Tyr Ser Phe Asn Ile Ser
                 85                  90                  95

Asn Leu Glu Pro Glu Asp Ile Ala Thr Tyr Tyr Cys Leu Gln Tyr Asp
                100                 105                 110

Asn Leu Trp Thr Phe Gly Gly Gly Thr Lys Leu Glu Ile Lys
             115                 120                 125

(2) INFORMATION FOR SEQ ID NO:3:

(i) SEQUENCE CHARACTERISTICS:
        (A) LENGTH: 470 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..420

(xi) SEQUENCE DESCRIPTION: SEQ ID NO:3:
```

```
ATG AAA TGC AGC TGG GTC ATG TTC TTC CTG ATG GCA GTG GTT ACA GGG      48
Met Lys Cys Ser Trp Val Met Phe Phe Leu Met Ala Val Val Thr Gly
 1               5                  10                  15

GTC AAT TCA GAG GTT CAG CTG CAG CAG TCT GGG GCA GAG CTT GTG AAG      96
Val Asn Ser Glu Val Gln Leu Gln Gln Ser Gly Ala Glu Leu Val Lys
                20                  25                  30

CCA GGG GCC TCA GTC AAG TTG TCC TGC ACA GCT TCT GGC TTC AAC ATT    144
Pro Gly Ala Ser Val Lys Leu Ser Cys Thr Ala Ser Gly Phe Asn Ile
            35                  40                  45

AAA GAC ACC TAT ATA CAC TGT GTG AAG CAG AGG CCT GAA CAG GGC CTG    192
Lys Asp Thr Tyr Ile His Cys Val Lys Gln Arg Pro Glu Gln Gly Leu
        50                  55                  60

GAG TGG ATT GGA AGG ATT GAT CCT GCG AAT GGT TAT ACT AAA TAT GAC    240
Glu Trp Ile Gly Arg Ile Asp Pro Ala Asn Gly Tyr Thr Lys Tyr Asp
 65                 70                  75                  80

CCG AAG TTC CAG GGC AAG GCC ACT ATA ACA GCT GAC ACA TCC TCC AAC    288
Pro Lys Phe Gln Gly Lys Ala Thr Ile Thr Ala Asp Thr Ser Ser Asn
                85                  90                  95

ACA GCC TAC CTG CAG CTC AGC AGC CTG ACA TCT GAG GAC ACT GCC GTC    336
Thr Ala Tyr Leu Gln Leu Ser Ser Leu Thr Ser Glu Asp Thr Ala Val
            100                 105                 110

TAT TTC TGT GCT AGA GAG GGA TAT TAT GGT AAC TAC GGG GTC TAT GCT    384
Tyr Phe Cys Ala Arg Glu Gly Tyr Tyr Gly Asn Tyr Gly Val Tyr Ala
        115                 120                 125

ATG GAC TAC TGG GGT CAA GGA ACC TCA GTC ACC GTC TCCTCAGCCA         430
Met Asp Tyr Trp Gly Gln Gly Thr Ser Val Thr Val
130                 135                 140

AAACGACACC CCCATCTGTC TATCCACTGG CCCGGGATCC                        470

(2) INFORMATION FOR SEQ ID NO:4:

(i) SEQUENCE CHARACTERISTICS:
        (A) LENGTH: 140 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Cys Ser Trp Val Met Phe Phe Leu Met Ala Val Val Thr Gly
 1               5                  10                  15

Val Asn Ser Glu Val Gln Leu Gln Gln Ser Gly Ala Glu Leu Val Lys
                20                  25                  30

Pro Gly Ala Ser Val Lys Leu Ser Cys Thr Ala Ser Gly Phe Asn Ile
            35                  40                  45

Lys Asp Thr Tyr Ile His Cys Val Lys Gln Arg Pro Glu Gln Gly Leu
        50                  55                  60

Glu Trp Ile Gly Arg Ile Asp Pro Ala Asn Gly Tyr Thr Lys Tyr Asp
 65                 70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Phe Cys Ala Arg Glu Gly Tyr Tyr Gly Asn Tyr Gly Val Tyr Ala
        115                 120                 125

Met Asp Tyr Trp Gly Gln Gly Thr Ser Val Thr Val
130                 135                 140

(2) INFORMATION FOR SEQ ID NO:5:
```

(i) SEQUENCE CHARACTERISTICS:
    (A) LENGTH: 106 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:5:

```
Asp Ile Gln Met Thr Gln Ser Pro Ser Ser Leu Ser Ala Ser Leu Gly
1               5                   10                  15

Gly Lys Val Thr Ile Thr Cys Lys Thr Ser Gln Asp Ile Asn Lys Tyr
            20                  25                  30

Met Ala Trp Tyr Gln His Lys Pro Gly Lys Arg Pro Arg Leu Leu Ile
        35                  40                  45

His Tyr Thr Ser Ala Leu Gln Pro Gly Ile Pro Ser Arg Phe Ser Gly
    50                  55                  60

Ser Gly Ser Gly Arg Asp Tyr Ser Phe Asn Ile Ser Asn Leu Glu Pro
65                  70                  75                  80

Glu Asp Ile Ala Thr Tyr Tyr Cys Leu Gln Tyr Asp Asn Leu Trp Thr
                85                  90                  95

Phe Gly Gly Gly Thr Lys Leu Glu Ile Lys
                100                 105
```

(2) INFORMATION FOR SEQ ID NO:6:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Asn Trp Tyr Gln Gln Thr Pro Gly Lys Ala Pro Lys Leu Leu Ile
        35                  40                  45

Tyr Glu Ala Ser Asn Leu Gln Ala Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Leu Gln Ile Thr
                100                 105
```

(2) INFORMATION FOR SEQ ID NO:7:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

```
Asp Ile Gln Met Thr Gln Ser Pro Ser Ser Leu Ser Ala Ser Val Gly
1               5                   10                  15

Asp Arg Val Thr Ile Thr Cys Lys Thr Ser Gln Asp Ile Asn Lys Tyr
            20                  25                  30

Met Ala Trp Tyr Gln Gln Thr Pro Gly Lys Ala Pro Arg Leu Leu Ile
        35                  40                  45

His Tyr Thr Ser Ala Leu Gln Pro Gly Ile Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Trp Thr
                85                  90                  95

Phe Gly Gln Gly Thr Lys Val Glu Ile Lys
            100                 105

(2) INFORMATION FOR SEQ ID NO:8:

(i) SEQUENCE CHARACTERISTICS:
        (A) LENGTH: 107 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Asn Trp Tyr Gln Gln Thr Pro Gly Lys Ala Pro Arg Leu Leu Ile
        35                  40                  45

Tyr Glu Ala Ser Asn Leu Gln Ala Gly Ile Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Leu Gln Ile Thr
            100                 105

(2) INFORMATION FOR SEQ ID NO:9:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Cys Val Lys Gln Arg Pro Glu Gln Gly Leu Glu Trp Ile
        35                  40                  45

Gly Arg Ile Asp Pro Ala Asn Gly Tyr Thr Lys Tyr Asp Pro Lys Phe
    50                  55                  60
```

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Ala Arg Glu Gly Tyr Tyr Gly Asn Tyr Gly Val Tyr Ala Met Asp Tyr
            100                 105                 110

Trp Gly Gln Gly Thr Ser Val Thr Val Ser Ser
        115                 120

(2) INFORMATION FOR SEQ ID NO:10:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
            100                 105                 110

Thr Leu Val Thr Val Ser Ser
        115

(2) INFORMATION FOR SEQ ID NO:11:

(i) SEQUENCE CHARACTERISTICS:
        (A) LENGTH: 123 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Thr
                20                  25                  30

Tyr Ile His Trp Val Arg Gln Ala Pro Gly Gln Arg Leu Glu Trp Met
            35                  40                  45

Gly Arg Ile Asp Pro Ala Asn Gly Tyr Thr Lys Tyr Asp Pro Lys Phe
        50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys

```
                    85                  90                  95
Ala Arg Glu Gly Tyr Tyr Gly Asn Tyr Gly Val Tyr Ala Met Asp Tyr
                100                 105                 110

Trp Gly Gln Gly Thr Leu Val Thr Val Ser Ser
        115                 120
```

(2) INFORMATION FOR SEQ ID NO:12:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Ser Tyr
                20                  25                  30

Ala Met His Trp Val Arg Gln Ala Pro Gly Gln Gly Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Tyr Gly Ser Gly Ser Asn Tyr Trp Gly Gln Gly
                100                 105                 110

Thr Leu Val Thr Val Ser Ser
        115
```

(2) INFORMATION FOR SEQ ID NO:13:

(i) SEQUENCE CHARACTERISTICS:
        (A) LENGTH: 119 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:13:

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
        50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Phe Gly Ser Gly Ser Asn Tyr Trp Gly Gln Gly
                100                 105                 110
```

Thr Leu Val Thr Val Ser Ser
       115

(2) INFORMATION FOR SEQ ID NO:14:

(i) SEQUENCE CHARACTERISTICS:
        (A) LENGTH: 406 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 16..393

(xi) SEQUENCE DESCRIPTION: SEQ ID NO:14:

```
AAGCTTGCCG CCACC ATG AGA CCG TCT ATT CAG TTC CTG GGG CTC TTG TTG         51
                 Met Arg Pro Ser Ile Gln Phe Leu Gly Leu Leu Leu
                  1               5                  10

TTC TGG CTT CAT GGT GCT CAG TGT GAC ATC CAG ATG ACA CAG TCT CCA          99
Phe Trp Leu His Gly Ala Gln Cys Asp Ile Gln Met Thr Gln Ser Pro
         15                  20                  25

TCC TCA CTG TCT GCA TCT CTG GGA GGC AAA GTC ACC ATC ACT TGC AAG         147
Ser Ser Leu Ser Ala Ser Leu Gly Gly Lys Val Thr Ile Thr Cys Lys
 30                  35                  40

ACA AGC CAA GAC ATT AAC AAG TAT ATG GCT TGG TAC CAA CAC AAG CCT         195
Thr Ser Gln Asp Ile Asn Lys Tyr Met Ala Trp Tyr Gln His Lys Pro
 45                  50                  55                  60

GGA AAA CGT CCT AGG CTG CTC ATA CAT TAC ACA TCT GCA TTA CAG CCA         243
Gly Lys Arg Pro Arg Leu Leu Ile His Tyr Thr Ser Ala Leu Gln Pro
                 65                  70                  75

GGC ATC CCA TCA AGG TTC AGT GGA AGT GGG TCT GGG AGA GAT TAT TCC         291
Gly Ile Pro Ser Arg Phe Ser Gly Ser Gly Ser Gly Arg Asp Tyr Ser
             80                  85                  90

TTC AAC ATC AGC AAC CTG GAG CCT GAA GAT ATT GCA ACT TAT TAT TGT         339
Phe Asn Ile Ser Asn Leu Glu Pro Glu Asp Ile Ala Thr Tyr Tyr Cys
         95                 100                 105

CTA CAG TAT GAT AAT CTG TGG ACG TTC GGT GGA GGC ACC AAG CTG GAA         387
Leu Gln Tyr Asp Asn Leu Trp Thr Phe Gly Gly Gly Thr Lys Leu Glu
 110                 115                 120

ATC AAA CGTGAGTGGA TCC                                                  406
Ile Lys
125
```

(2) INFORMATION FOR SEQ ID NO:15:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:15:

```
Met Arg Pro Ser Ile Gln Phe Leu Gly Leu Leu Leu Phe Trp Leu His
 1               5                  10                  15

Gly Ala Gln Cys Asp Ile Gln Met Thr Gln Ser Pro Ser Ser Leu Ser
             20                  25                  30

Ala Ser Leu Gly Gly Lys Val Thr Ile Thr Cys Lys Thr Ser Gln Asp
         35                  40                  45

Ile Asn Lys Tyr Met Ala Trp Tyr Gln His Lys Pro Gly Lys Arg Pro
 50                  55                  60
```

```
Arg Leu Leu Ile His Tyr Thr Ser Ala Leu Gln Pro Gly Ile Pro Ser
 65                  70                  75                  80

Arg Phe Ser Gly Ser Gly Ser Gly Arg Asp Tyr Ser Phe Asn Ile Ser
                 85                  90                  95

Asn Leu Glu Pro Glu Asp Ile Ala Thr Tyr Tyr Cys Leu Gln Tyr Asp
             100                 105                 110

Asn Leu Trp Thr Phe Gly Gly Gly Thr Lys Leu Glu Ile Lys
             115                 120                 125
```

(2) INFORMATION FOR SEQ ID NO:16:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 16..441

(xi) SEQUENCE DESCRIPTION: SEQ ID NO:16:

```
AAGCTTGCCG CCACC ATG GAC TGG ACC TGG CGC GTG TTT TGC CTG CTC GCC        51
                 Met Asp Trp Thr Trp Arg Val Phe Cys Leu Leu Ala
                  1               5                  10

GTG GCT CCT GGG GCC CAC AGC CAG GTG CAA CTA GTG CAG TCC GGC GCC         99
Val Ala Pro Gly Ala His Ser Gln Val Gln Leu Val Gln Ser Gly Ala
             15                  20                  25

GAA GTG AAG AAA CCC GGT GCT TCC GTG AAA GTC AGC TGT AAA GCT AGC        147
Glu Val Lys Lys Pro Gly Ala Ser Val Lys Val Ser Cys Lys Ala Ser
 30                  35                  40

GGT TTC AAC ATT AAA GAC ACC TAT ATA CAC TGG GTT AGA CAG GCC CCT        195
Gly Phe Asn Ile Lys Asp Thr Tyr Ile His Trp Val Arg Gln Ala Pro
 45                  50                  55                  60

GGC CAA AGG CTG GAG TGG ATG GGA AGG ATT GAT CCT GCG AAT GGT TAT        243
Gly Gln Arg Leu Glu Trp Met Gly Arg Ile Asp Pro Ala Asn Gly Tyr
             65                  70                  75

ACT AAA TAT GAC CCG AAG TTC CAG GGC CGG GTC ACC ATC ACC GCA GAC        291
Thr Lys Tyr Asp Pro Lys Phe Gln Gly Arg Val Thr Ile Thr Ala Asp
                 80                  85                  90

ACC TCT GCC AGC ACC GCC TAC ATG GAA CTG TCC AGC CTG CGC TCC GAG        339
Thr Ser Ala Ser Thr Ala Tyr Met Glu Leu Ser Ser Leu Arg Ser Glu
             95                 100                 105

GAC ACT GCA GTC TAC TAC TGC GCC AGA GAG GGA TAT TAT GGT AAC TAC        387
Asp Thr Ala Val Tyr Tyr Cys Ala Arg Glu Gly Tyr Tyr Gly Asn Tyr
110                 115                 120

GGG GTC TAT GCT ATG GAC TAC TGG GGT CAA GGA ACC CTT GTC ACC GTC        435
Gly Val Tyr Ala Met Asp Tyr Trp Gly Gln Gly Thr Leu Val Thr Val
125                 130                 135                 140

TCC TCA GGTGAGTGGA TCC                                                 454
Ser Ser
```

(2) INFORMATION FOR SEQ ID NO:17:

(i) SEQUENCE CHARACTERISTICS:
        (A) LENGTH: 142 amino acids
        (B) TYPE: amino acid
        (D) TOPOLOGY: linear (ii) MOLECULE TYPE: protein (xi) SEQUENCE DESCRIPTION: SEQ ID NO:17:

Met Asp Trp Thr Trp Arg Val Phe Cys Leu Leu Ala Val Ala Pro Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Phe Asn Ile
        35                  40                  45

Lys Asp Thr Tyr Ile His Trp Val Arg Gln Ala Pro Gly Gln Arg Leu
    50                  55                  60

Glu Trp Met Gly Arg Ile Asp Pro Ala Asn Gly Tyr Thr Lys Tyr Asp
65              70                  75                  80

Pro Lys Phe Gln Gly Arg Val Thr Ile Thr Ala Asp Thr Ser Ala Ser
            85                  90                  95

Thr Ala Tyr Met Glu Leu Ser Ser Leu Arg Ser Glu Asp Thr Ala Val
        100                 105                 110

Tyr Tyr Cys Ala Arg Glu Gly Tyr Tyr Gly Asn Tyr Gly Val Tyr Ala
    115                 120                 125

Met Asp Tyr Trp Gly Gln Gly Thr Leu Val Thr Val Ser Ser
130                 135                 140

(2) INFORMATION FOR SEQ ID NO:18:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:18:

CAGAAAGCTT GCCGCCACCA TGAGACCGTC TATTCAG                                37

(2) INFORMATION FOR SEQ ID NO:19:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:19:

CCGAGGATCC ACTCACGTTT GATTTCCAGC TTGGT                                  35

(2) INFORMATION FOR SEQ ID NO:20:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:20:

CAGAAAGCTT GCCGCCACCA TGAAATGCAG CTGGGTC                                37

(2) INFORMATION FOR SEQ ID NO:21:

(i) SEQUENCE CHARACTERISTICS:
        (A) LENGTH: 33 base pairs (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:21:

CCGAGGATCC ACTCACCTGA GGAGACGGTG ACT                                    33

(2) INFORMATION FOR SEQ ID NO:22:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:22:

GATGGTGACT CTATCTCCTA CAGATGCAGA CAGTGAGGA                              39

(2) INFORMATION FOR SEQ ID NO:23:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:23:

CTGTAGGAGA TAGAGTCACC ATCACTTGCA AG                                     32

(2) INFORMATION FOR SEQ ID NO:24:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:24:

AGGAGCTTTT CCAGGTGTCT GTTGGTACCA AGCCATATA                              39

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:25:

ACCAACAGAC ACCTGGAAAA GCTCCTAGGC TGCTCATACA T                           41

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:26:

GCAGGCTGCT GATGGTGAAA GTATAATCTC TCCCAGACCC                    40

(2) INFORMATION FOR SEQ ID NO:27:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:27:

ACTTTCACCA TCAGCAGCCT GCAGCCTGAA GATATTGCAA CT                 42

(2) INFORMATION FOR SEQ ID NO:28:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:28:

CCGAGGATCC ACTCACGTTT GATTTCCACC TTGGTGCCTT GACCGAACGT CCACAGATT    59

(2) INFORMATION FOR SEQ ID NO:29:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:29:

GGAAAAGCTC CTAGGCTGCT CATATATTAC ACA                           33

(2) INFORMATION FOR SEQ ID NO:30:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:30:

CCGAGGATCC ACTCACGTTT GATTTCCACC TTTGTGCC                      38

(2) INFORMATION FOR SEQ ID NO:31:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:31:

```
AACCCAGTGT ATATAGGTGT CTTTAATGTT GAAACCGCTA GCTTTACAGC T           51
```

(2) INFORMATION FOR SEQ ID NO:32:

(i) SEQUENCE CHARACTERISTICS:
        (A) LENGTH: 67 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:32:

```
AAAGACACCT ATATACACTG GGTTAGACAG GCCCCTGGCC AAAGGCTGGA GTGGATGGGA   60
AGGATTG                                                            67
```

(2) INFORMATION FOR SEQ ID NO:33:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:33:

```
GACCCGGCCC TGGAACTTCG GGTCAT                                       26
```

(2) INFORMATION FOR SEQ ID NO:34:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:34:

```
GACCCGAAGT TCCAGGGCAG GGTCACCATC ACCGCAGACA CCTCTGCCAG CACCGCCTAC   60
ATGGAA                                                             66
```

(2) INFORMATION FOR SEQ ID NO:35:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:35:

```
CCATAGCATA GACCCCGTAG TTACCATAAT ATCCCTCTCT GGCGCAGTAG TAGACTGCAG   60
TGTC                                                               64
```

(2) INFORMATION FOR SEQ ID NO:36:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: DNA (primer)

-continued

```
    (xi) SEQUENCE DESCRIPTION: SEQ ID NO:36:

GGTAACTACG GGGTCTATGC TATGGACTAC TGGGGTCAAG GAACCCTTGT CACCGTCTCC      60

TCA                                                                   63

(2) INFORMATION FOR SEQ ID NO:37:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:37:

CCAGGGCCGG GTCACCATCA CCAGAGACAC CTCTGCC                              37

(2) INFORMATION FOR SEQ ID NO:38:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:38:

CAGGCCCCTG GCCAAGGGCT GGAGTGG                                         27

(2) INFORMATION FOR SEQ ID NO:39:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:39:

TACGCAAACC GCCTCTC                                                    17

(2) INFORMATION FOR SEQ ID NO:40:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (primer)

(xi) SEQUENCE DESCRIPTION: SEQ ID NO:40:

GAGTGCACCA TATGCGGT                                                   18

(2) INFORMATION FOR SEQ ID NO:41:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Ser Tyr
            20                  25                  30

Tyr Ile His Trp Val Arg Gln Ala Pro Gly Gln Gly Leu Glu Trp Val
            35                  40                  45

Gly Tyr Ile Asp Pro Phe Asn Gly Gly Thr Ser Tyr Asn Gln Lys Phe
50                  55                  60

Lys Gly Lys Val Thr Met Thr Val Asp Thr Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Asn Arg Phe Ala Tyr Trp Gly Gln Gly Thr Leu Val
            100                 105                 110

Thr Val Ser Ser
        115

(2) INFORMATION FOR SEQ ID NO:42:

(i) SEQUENCE CHARACTERISTICS:
        (A) LENGTH: 109 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Asn
            20                  25                  30

Tyr Leu Asn Trp Tyr Gln Gln Lys Pro Gly Ser Pro Lys Leu Leu
35                  40                  45

Ile Tyr Tyr Ala Ser Arg Leu His Ser Gly Val Pro Ser Arg Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Pro Arg Thr Phe Gly Gly Gly Thr Lys Leu Glu Ile Lys
            100                 105

(2) INFORMATION FOR SEQ ID NO:43:

(i) SEQUENCE CHARACTERISTICS:
        (A) LENGTH: 114 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ser Leu Val Xaa
            20                  25                  30

Xaa Ser Ile Ser Asn Tyr Leu Asn Trp Tyr Gln Gln Lys Pro Gly Lys
35                  40                  45
```

```
Ala Pro Lys Leu Leu Ile Tyr Ala Ala Ser Ser Leu Glu Ser Gly Val
     50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Phe Ala Thr Tyr Tyr Cys Gln Gln
                 85                  90                  95

Tyr Asn Ser Leu Pro Gly Trp Thr Phe Gly Gln Gly Thr Lys Val Glu
                100                 105                 110

Ile Lys (2) INFORMATION FOR SEQ ID NO:44:

(i) SEQUENCE CHARACTERISTICS:
        (A) LENGTH: 125 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

Glu Val Gln Leu Gln Gln Ser Gly Ala Glu Leu Val Lys Pro Gly Ala
 1               5                  10                  15

Ser Val Lys Leu Ser Cys Thr Ala Ser Gly Phe Asn Ile Lys Asp Thr
                 20                  25                  30

Tyr Met His Trp Val Lys Gln Arg Pro Glu Gln Gly Leu Glu Trp Ile
                 35                  40                  45

Gly Arg Ile Asp Pro Ala Asn Gly Asn Thr Lys Tyr Asp Pro Lys Phe
     50                  55                  60

Gln Gly Lys Ala Thr Ile Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                 85                  90                  95

Ala Arg Gly Tyr Tyr Tyr Tyr Asp Ser Xaa Val Gly Tyr Tyr Ala Met
                100                 105                 110

Asp Tyr Trp Gly Gln Gly Thr Xaa Val Thr Val Ser Ser
                115                 120                 125

(2) INFORMATION FOR SEQ ID NO:45:

(i) SEQUENCE CHARACTERISTICS:
        (A) LENGTH: 129 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Ala Ile Ser Trp Val Arg Gln Ala Pro Gly Gln Gly Leu Glu Trp Met
                 35                  40                  45

Gly Trp Ile Asn Pro Tyr Gly Asn Gly Asp Thr Asn Tyr Ala Gln Lys
     50                  55                  60

Phe Gln Gly Arg Val Thr Ile Thr Ala Asp Thr Ser Thr Ser Thr Ala
 65                  70                  75                  80
```

```
Tyr Met Glu Leu Ser Ser Leu Arg Ser Glu Asp Thr Ala Val Tyr Tyr
                85                  90                  95

Cys Ala Arg Ala Pro Gly Tyr Gly Ser Gly Gly Gly Cys Tyr Arg Gly Asp
            100             105                 110

Tyr Xaa Phe Asp Tyr Trp Gly Gln Gly Thr Leu Val Thr Val Ser Ser
    115             120             125
```